(12) United States Patent
Perez et al.

(10) Patent No.: US 9,095,611 B1
(45) Date of Patent: Aug. 4, 2015

(54) SYNTHESIS OF HYPERBRANCHED AMPHIPHILIC POLYESTER AND THERANOSTIC NANOPARTICLES THEREOF

(71) Applicant: University of Central Florida Research Foundation, Inc., Orlando, FL (US)

(72) Inventors: J Manuel Perez, Orlando, FL (US); Santimukal Santra, Orlando, FL (US)

(73) Assignee: The University of Central Florida Research Foundation, Inc., Orlando, FL (US)

( * ) Notice: Subject to any disclaimer, the term of this patent is extended or adjusted under 35 U.S.C. 154(b) by 63 days.

(21) Appl. No.: 13/626,955

(22) Filed: Sep. 26, 2012

Related U.S. Application Data

(62) Division of application No. 12/417,017, filed on Apr. 2, 2009, now Pat. No. 8,372,944.

(60) Provisional application No. 61/041,624, filed on Apr. 2, 2008.

(51) Int. Cl.
| | |
|---|---|
| *C08G 63/00* | (2006.01) |
| *C07C 61/00* | (2006.01) |
| *C07C 27/10* | (2006.01) |
| *A61K 49/00* | (2006.01) |
| *A61K 9/14* | (2006.01) |
| *A61K 31/505* | (2006.01) |
| *A61K 9/16* | (2006.01) |
| *C08G 63/06* | (2006.01) |

(52) U.S. Cl.
CPC ......... *A61K 49/0032* (2013.01); *A61K 49/0093* (2013.01); *A61K 9/146* (2013.01); *A61K 9/1647* (2013.01); *A61K 31/505* (2013.01); *C08G 63/06* (2013.01)

(58) Field of Classification Search
CPC .................. A61K 2201/023; A61K 49/0032; A61K 49/0093; A61K 9/5153; A61K 9/5192; A61K 31/505; A61K 9/1647; A61K 9/146; C08G 63/06

USPC .......... 528/271, 361, 397; 562/400; 424/501; 514/50, 772.3, 784, 785

See application file for complete search history.

(56) References Cited

U.S. PATENT DOCUMENTS 6,444,758 B2  9/2002  McNamara et al.

OTHER PUBLICATIONS

Jayakannan et al., Preparation of polyethers via proton acid catalyzed transetherification reactions, Macromol. Chem. Phys. , 201, pp. 759-767, Sep. 20, 1999.

Malmstrom et al., Hyperbranched Aliphatic Polyesters, Macromolecules, 28, pp. 1698-1703, 2005.

Ault, Techniques and Experiments for Organic Chemistry, Sixth Edition, copyright 1998, pp. 48-50, 53-55, 60, 130-131.

Santra et al., Facile synthesis of aliphatic hyperbranched polyesters based on diethyl malonate and their irreversible molecular encapsulation, Chemical Communications, pp. 2126-2127, Jul. 29, 2004.

*Primary Examiner* — Richard Schnizer
*Assistant Examiner* — Alma Pipic
(74) *Attorney, Agent, or Firm* — Ballard Spahr LLP

(57) ABSTRACT

A method of making a hyperbranched amphiphilic polyester compound includes drying under vacuum a mixture of 2-(4-hydroxybutyl)-malonic acid and p-toluene sulphonic acid as catalyst. The vacuum is then released with a dry inert gas after drying. The dried mixture is heated under the inert gas at a temperature sufficient for polymerization. The inert gas is evacuated while continuing to heat the mixture. The formed polymer is then dissolved in dimethylformamide and precipitated out by adding methanol. Modifications of the method yield nanoparticles of polyesters having properties suited for coencapsulating fluorescent dyes together with therapeutic drugs, resulting in theranostic nanoparticles, that is, nanoparticles useful in both therapeutic treatments and diagnostic methods.

17 Claims, 29 Drawing Sheets
(16 of 29 Drawing Sheet(s) Filed in Color)

SYNTHESIS OF HYPERBRANCHED AMPHIPHILIC POLYESTER AND THERANOSTIC NANOPARTICLES THEREOF

CROSS-REFERENCE TO RELATED APPLICATIONS

This is a division of application Ser. No. 12/417,017 filed Apr. 2, 2009, entitled "Synthesis of Hyperbranched Amphiphilic Polyester and Theranostic Particles Thereof," which claims the benefit of provisional application Ser. No. 61/041,624 filed on Apr. 2, 2008. Both of these applications are incorporated herein by reference in their entireties.

STATEMENT OF GOVERNMENT RIGHTS

This invention was made with government support under CA101781 awarded by the National Institutes of Health. The government has certain rights in the invention.

FIELD OF THE INVENTION

The present invention relates to the field of nanotechnology and, more particularly, to nanoparticles useful as carriers of fluorescent dyes for diagnostic purposes and therapeutic drugs for treatment of disease; these dual-purpose particles are also known as "theranostic nanoparticles."

BACKGROUND OF THE INVENTION

Polymer science has traditionally focused on linear polymers or cross-linked linear polymers, resulting in a wide variety of materials implemented in most facets of daily life. Recent progress in polymer sciences has resulted in the development of dendrimers1 and most recently hyperbranched polymers2-4 consisting of branched structures with high numbers of reactive groups in their periphery. The syntheses of these multifunctional dendritic (branched) polymers hold great promise for targeted delivery of drugs, therapeutics, diagnostics and imaging. The perfectly branched structures called dendrimers are constructed by an iterative and complex reaction sequence involving protection-deprotection steps whereas hyperbranched polymers, the less perfect structures, are made by one step polymerization reaction. Recent advances in nonviral drug delivery and cancer chemotherapy have revealed biocompatible branched polymers like polyethyleneimine (PEI) and starburst PAMAM as effective drug delivery systems, which can mimic naturally occurring biological transport systems such as lipoproteins and viruses.5 Unlike linear polymers which are produced from divalent AB type monomers, dendritic macromolecules are produced from polyvalent ABn monomers (n≥2), giving rise to its branching and multiple-end structures.6-8 Dendritic polymers have gained large interest in recent years because of their highly branched structures facilitating effective encapsulation of guest molecules and having many attractive features such as improved solubility, reactivity, structure architecture, biocompatibility, low viscosity and low crystallinity compared to those of linear polymers of same molecular weight.9 Therefore, the creation of new and highly branched polymeric nanostructures with multifunctional capabilities is central to the development of novel materials with applications in various fields ranging from drug delivery, immunoassays, microelectrons, coating and nanocomposites.10,11 Polymeric nanoparticles and nanocomposites with dual fluorescent, magnetic and therapeutic properties will have a huge impact in medicine, particularly in cancer diagnosis and treatment, where novel targeted multifunctional polymeric nanoparticles can be developed to obtained spatiotemporal information about disease stage and progress of a therapeutic regime.12-14 Hence, there has been substantial interest in developing smart therapeutic and selective polymeric vehicles for targeted treatment of various diseases, preventing toxicity to healthy tissues.

SUMMARY OF THE INVENTION

With the foregoing in mind, the present invention advantageously provides methods for maing hyperbranched amphiphilic polyester compounds. These polyesters may be used to generate nanoparticles having one or more hydrophobic pockets and a hydrophilic outer surface. The polymeric nanoparticles (PNPs) may be used as carriers for a hydrophobic near-infrared fluorescent dye and/or a therapeutic drug. The PNPs are biodegradable and, having been modified with appropriate chemical groups along their outer surface, are readily taken into cells, thus providing an ideal vehicle for delivery of therapeutic drugs. Since the PNPs may carry both a fluorescent dye and a therapeutic drug, they can be tracked optically via the dye and simultaneously deliver the drug to predetermined cells. The capability of having both a therapeutic modality and a diagnostic modality may be identified as "theranostic."

A method of the present invention includes making a hyperbranched amphiphilic polyester compound. The method includes drying under vacuum a mixture of 2-(4-hydroxybutyl)-malonic acid and p-toluene sulphonic acid as catalyst. Then, releasing the vacuum with a dry inert gas after drying. The method continues by heating the dried mixture under the inert gas at a temperature sufficient for polymerization. The method proceeds by evacuating the inert gas while continuing to heat the mixture, then dissolving the formed polymer in dimethylformamide. Finally, the method ends after precipitating the dissolved polymer by adding methanol.

In the method, drying may comprise a mixture of 2-(4-hydroxybutyl)-malonic acid and p-toluene sulphonic acid in approximately a 100:1 molar ratio. Also, drying under vacuum preferably comprises a high vacuum and the inert gas is argon gas. The heating is preferably at a temperature of approximately 150° C., which promotes polymerization. The heating may continue for approximately two hours. Evacuating is most preferably conducted slowly at approximately 0.2 mm/Hg for about one hour while maintaining the polymerization temperature. After polymerization, the method may further comprise purifying the polymer by separating the precipitate, washing it with methanol and drying it in a vacuum.

The described method may be modified to make aminated PNPs. This is accomplished by dissolving the precipitated polymer in anhydrous dimethylformamide (DMF), adding 1,1'-carbonyldiimidazole drop-wise to form a reaction mixture and incubating the reaction mixture at room temperature for approximately one to two hours. This method continues by adding ethylenediamine in anhydrous DMF drop-wise and continue incubation of the reaction mixture at room temperature for approximately 24 hours, then precitipating the reaction mixture in methanol, separating the precipitate and drying in a vacuum to obtain a purified hyperbranched polyester amine.

Yet another modification of the described method is useful for making propargylated PNPs. This modification includes dissolving the precipitated polymer in anhydrous dimethylformamide (DMF), adding 1,1'-carbonyldiimidazole drop-wise to form a reaction mixture, incubating the reaction mixture at room temperature for approximately one to two hours, then adding propargyl chloride in anhydrous DMF drop-wise and continue incubation of the reaction mixture at room temperature for approximately 24 hours. Lastly, the method calls for precitipating the reaction mixture in methanol, separating the precipitate and drying in a vacuum to obtain a purified hyperbranched propargylated polyester amine.

Having described the method and its two modifications, the polymers generated thereby represent novel molecules useful at least for making the PNPs of the invention. Accordingly, the invention includes a polymer comprising the repeating unit HBPE (5).

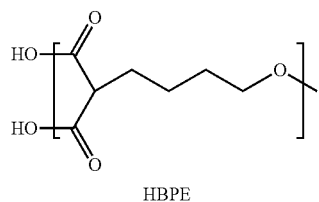

HBPE (5)

The invention additionally includes a polymeric nanoparticle comprising the polymer HBPE(5), the nanoparticle also having a hydrophobic near-infrared fluorescent dye encapsulated therein. The dye may be selected from the group consisting of DiI, DiR, and DiD. Additionally, this PNP may include a therapeutic drug coencapsulated with said fluorescent dye, and particularly, an anti-cancer drug such as azidothymidine.

Another polymer included in the invention is one comprising the repeating unit HBPE-EDA (6).

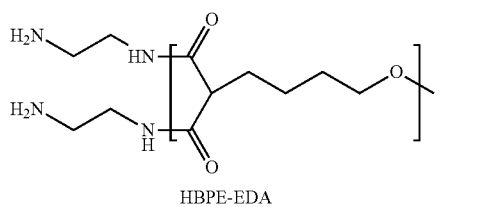

HBPE-EDA (6)

Moreover, the invention further includes a polymeric nanoparticle comprising the polymer HBPE-EDA(6) and a hydrophobic near-infrared fluorescent dye encapsulated therein. As noted above, the dye may be selected from the group consisting of DiI, DiR, and DiD, and the PNP may also include a therapeutic drug coencapsulated with said fluorescent dye.

The other modification of the presently disclosed method is useful for making a polymer comprising the repeating unit HBPE-PA(7), as set forth below.

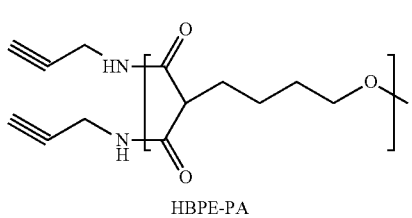

HBPE-PA (7)

Included in the invention is a polymeric nanoparticle comprising the polymer HBPE-PA(7) and a hydrophobic near-infrared fluorescent dye encapsulated therein. In this polymeric nanoparticle the dye may be selected from the group consisting of DiI, DiR, and DiD, and there may also be a therapeutic drug coencapsulated with said fluorescent dye. The therapeutic drug preferably comprises an anti-cancer drug, for example, azidothymidine or 25, wherein the anti-cancer comprises paclitaxel.

Those skilled in the art will recognize that while certain hydrophobic near-infrared fluorescent dyes have been given as examples, other dyes having similar properties would also be useful in the invention. The same can be expected to hold for therapeutic drugs other than the ones given here as examples; as long as the drug exhibits sufficient hydrophobicity to nest in the hydrophobic pocket formed by the polymer in the nanoparticle, the drug should be of use in the invention. These dyes and drugs as known to the skilled by their properties are, therefore, intended to be included within the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

Figure 1:
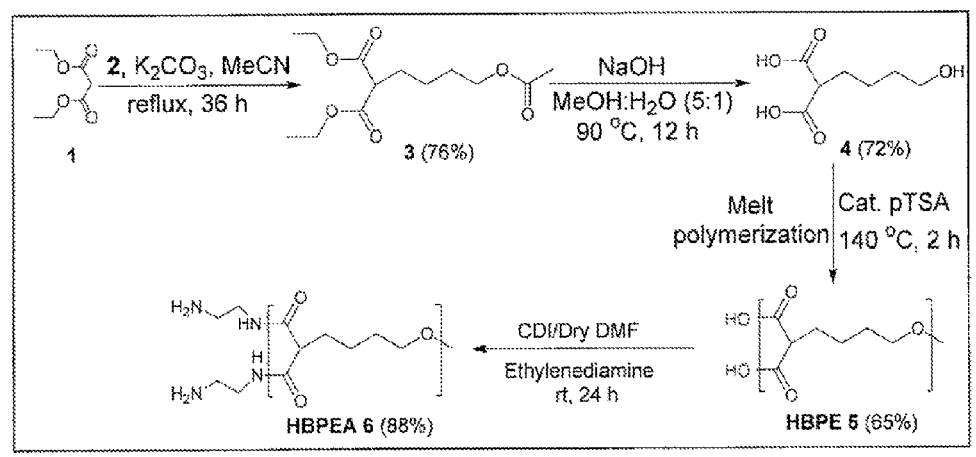
FIG. 1 illustrates, according to a method of the invention, the facile synthesis of amphiphilic hyperbranched polyester (HBPE, 5) and corresponding polyester-amine (HBPEA, 6) polymer, which are highly branched, globular, and biodegradable in nature; the polymeric backbone of HBPE was synthesized by melt polymerization of the monomer 4, which can be easily made from commercially available diethylmalonate 1 and bromobutyl acetate (2) in two simple steps, hence the synthesis of 5 is cost-effective; the corresponding aminated polymer can be synthesized via conjugation of ethylenediamine using 1,1'-carbonyldiimidazile (CDI) coupling; the resulting amphiphilic and dendritic polymers (5 and 6) contain inner hydrophobic domain (aliphatic chains), surrounded by a hydrophilic outer shell (carboxylic or amine groups), which after self assembly in water result in a stable nanoparticle suspension which can encapsulate hydrophobic dyes and drugs.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Herein, we report the synthesis of novel biodegradable hyperbranched polyesters and their use for the synthesis of cell-permeable polymeric nanoparticles that encapsulate hydrophobic dyes and drugs for dual optical imaging and therapeutic applications. To this date, no one has made biocompatible polymeric nanoparticles from diethylmalonate based hyperbranched polyester. The design and synthesis of diethylmalonate-based $AB_2$ monomer is novel and tuned in such a way that the resulting polymer will have three-dimensional molecular architecture with hydrophobic interior and hydrophilic segments at the surface (amphiphilic). Selective mono-C-alkylation of diethylmalonate using a mild basic condition and followed by hydrolysis of the monomer was performed to develop a new, water-soluble $AB_2$ monomer for the synthesis of the hyperbranched polyester. We have employed a melt polymerization technique using para-toluenesulfonic acid [p-TSA] as a catalyst to synthesize the novel aliphatic and biodegradable hyperbranched polyester. We hypothesized that the presence of $AB_2$ branching point and a hydrophobic butyl chain in the monomer structure could be able to generate a highly branched and hydrophobic polymer. As a proof-of-principle, the resulting polyester was highly branched, amphiphilic, having carboxylic acid groups at the surface and obtaining a three dimensional architecture with hydrophobic cavity. Therefore, compare to the conventional linear polymers, our branched polyester is amorphous, amphiphilic, soluble, biodegradable, highly surface functional and has cavities for effective encapsulation of guest molecules, which suggest its versatility in biomedical applications. Post-functionalization of this water insoluble polyester has been done using carbodiimide chemistry resulting in cationic and clickable hyperbranched polyester.

A solvent diffusion method has been adopted for the synthesis of polymeric nanoparticles (PNPs) where the hydrophobic areas assemble together to minimize contact with the aqueous environment, while exposing the hydrophilic segments containing carboxylic groups at the surface in aqueous solution.[15,16] This results in the formation of carboxyl functionalized spherical polymeric nanoparticles in water containing inner hydrophobic domains that can encapsulate hydrophobic molecules such as dyes and drugs.[17] Note that, this is the first example of development of hyperbranched polyester based polymeric nanoparticles using solvent diffusion method. Experimental data showed the effective encapsulation of various hydrophobic near infrared (NIR) dyes and a therapeutic drug without significant precipitation or reduction of the fluorescent properties. The fluorescence of the resulting PNPs is bright and stable, allowing the imaging of cells without significant photo-bleaching. Click chemistry has been used for the synthesis of folate decorated PNPs for the targeted cancer therapy.[18-20] Finally, we have been able to encapsulate either a hydrophobic antitumor drug (Paclitaxel) or, a nucleoside analog reverse transcriptase inhibitor (AzT) for the treatment of HIV and AIDS, along with near infra red fluorescent dyes (DiI or DiR) into the folate decorated PNPs for targeted drug delivery and imaging. We have used human lung carcinoma (A549) and normal cardiomyocites (h9c2) cell lines throughout all in vitro studies. We have assessed MTT assay to determine the cytotoxity of our functional PNPs. Results showed Taxol® and AzT encapsulated PNPs were toxic to the cancerous cell lines, whereas, dye encapsulated polymeric fluorophores were non-toxic. These results were corroborated with confocal microscopic studies and FACS analysis. The PNPs degradation and controlled drug and dye release experiments were performed under enzymatic and low pH environments. Most importantly, we are successful in animal imaging using mice model, in vivo, with the NIR dye (DiR and DiD) encapsulated PNPs for animal imaging applications.

Therefore, our present protocol is capable of creating a library of multifunctional therenostic (therapeutics and optical diagnostics) polymeric nanoparticles for biomedical applications including (a) encapsulated chemotherapeutic agents (Taxol® and AzT) for HIV and cancer therapy, (b) surface functionality (folic acid ligand) for cancer targeting, (c) "click"-chemistry-based conjugation of targeting ligands, (d) encapsulated NIR dyes for fluorescent imaging capabilities and (e) thermomechanical applications including luminescent, conductive, magnetic or radioprotection of the corresponding polymeric-metallic nanocomposites.

Results and Discussion

Synthesis and Characterization of Biodegradable Hyperbranched Polymers

Figure 2:
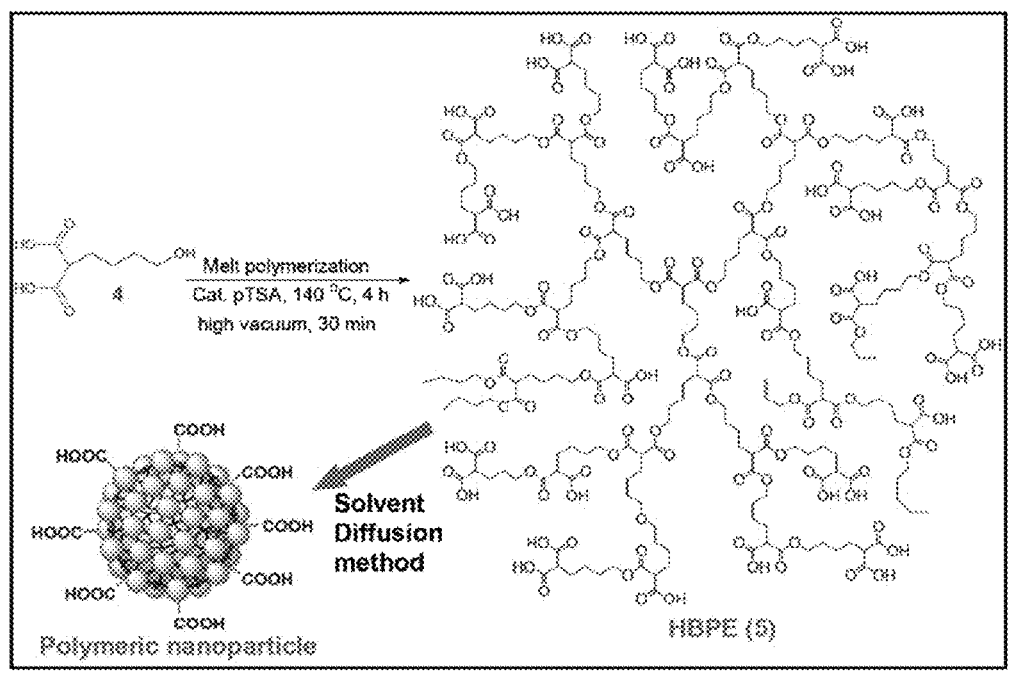
FIG. 2 shows a schematic representation of the structure of dendritic polyester (HBPE 5) and corresponding formation of polymeric nanoparticles via solvent diffusion method; using this method, a series of hydrophobic drugs and dyes can be encapsulated in one pot; these polymeric nanoparticles are highly dispersed in water and stable in a wide range of buffered solutions under physiological conditions; both click chemistry, carbodiimide chemistry and other conjugation chemistries can be used for the functionalization of these polymeric nanoparticles with small molecule like antibodies, proteins, oligonucleotides and other targeting agents to generate a nanoparticle-ligand library.
Figure 3:
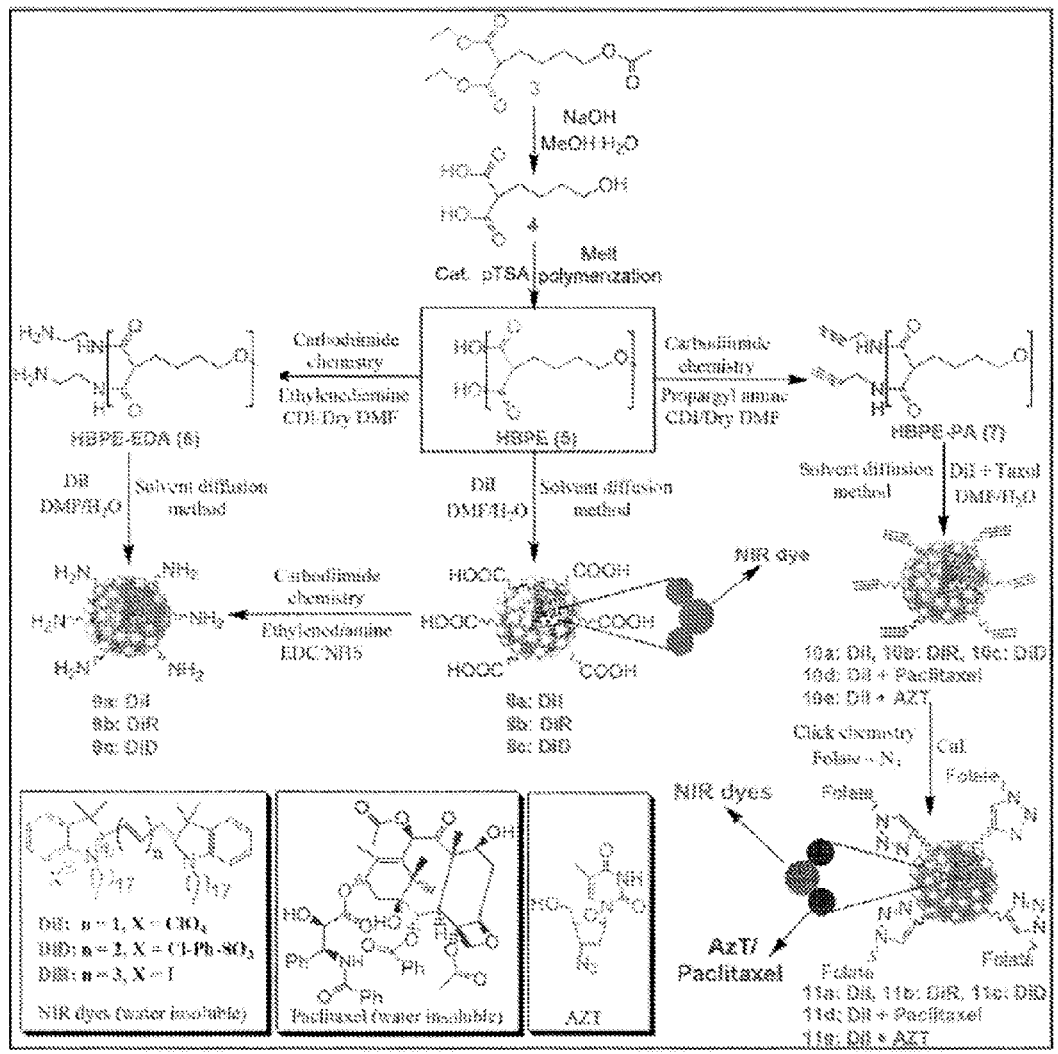
FIG. 3 presents an overall schematic representation of the preparation of functional polymers and polymeric nanoparticles (PNPs); polymer 5 was synthesized following the melt polymerization technique; PNPs were synthesized using the solvent diffusion method and were stable in water and other aqueous buffer solutions; carbodiimide chemistry has been followed for the synthesis of functional polymers (6 and 7) using 1,1'-carbonyldiimidazole (CDI), as a water insoluble carbodiimide. Near IR dyes (DiI, DiD and DiR), paclitaxel and AzT encapsulated PNPs were prepared in water from the water insoluble functional polymers using the solvent diffusion method. Click chemistry and carbodiimide chemistry has been used for the synthesis of a library of functional PNPs; insets show the structures of NIR dyes, Paclitaxel and AzT.
Figure 4:
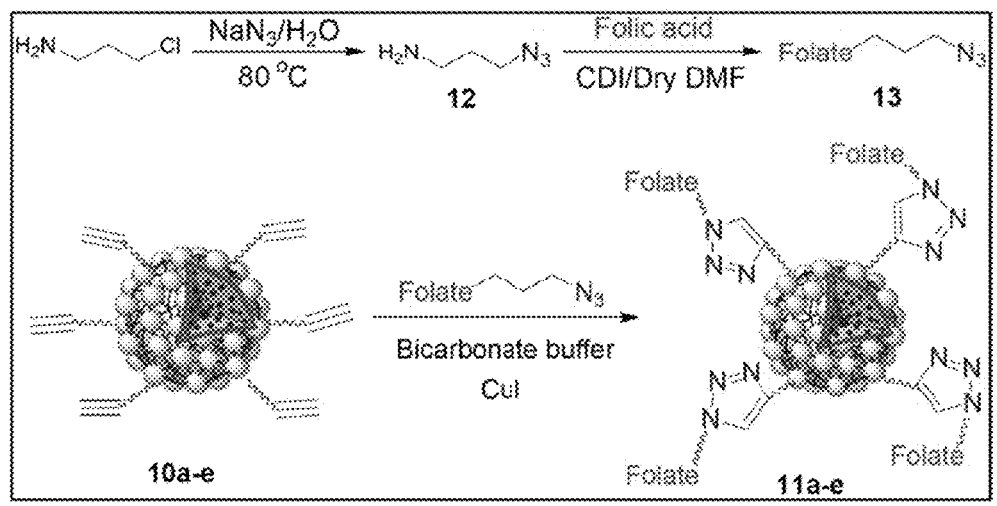
FIG. 4 is a representation of the synthesis of azide-functionalized folic acid (13) from chloropropylamine and CuI-catalyzed "click" chemistry for the preparation of folate-functionalized PNPs (11a-e)
Figure 5:
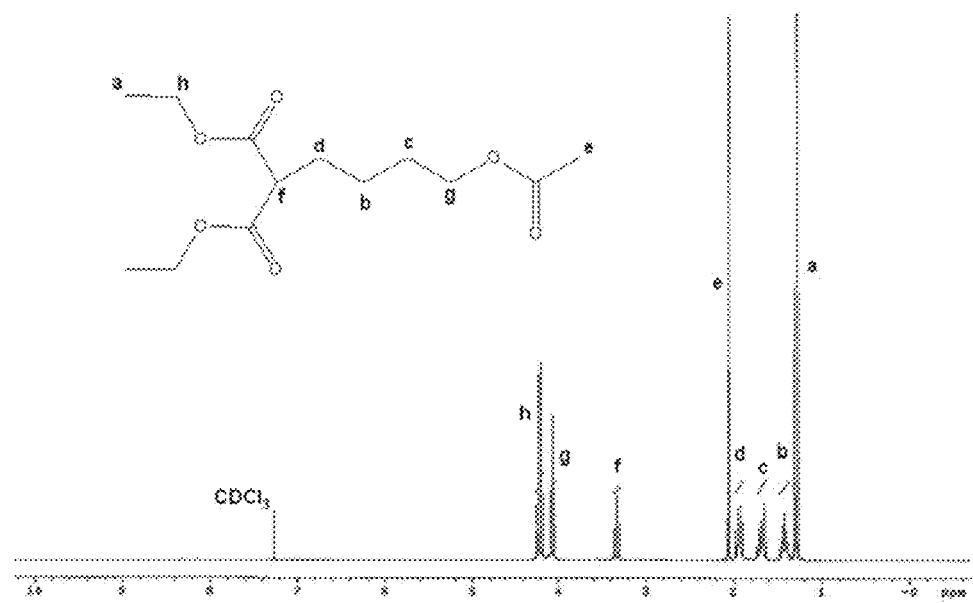
FIG. 5 shows $^1$H NMR spectrum of the AB2 monomer (3); the characteristic triplet for the single acidic proton (f) was observed at 3.34 ppm.
Figure 6:
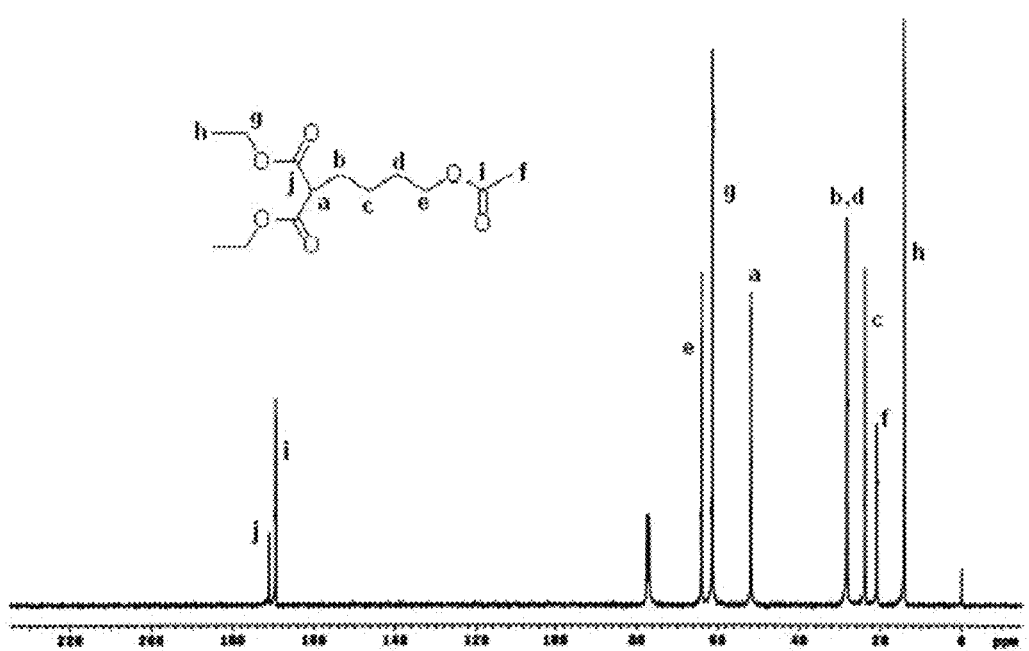
FIG. 6 depicts a $^{13}$C NMR spectrum of the AB2 monomer (3); all peaks are assigned to the corresponding carbons, which confirms the presence of the expected compound.
Figure 7:
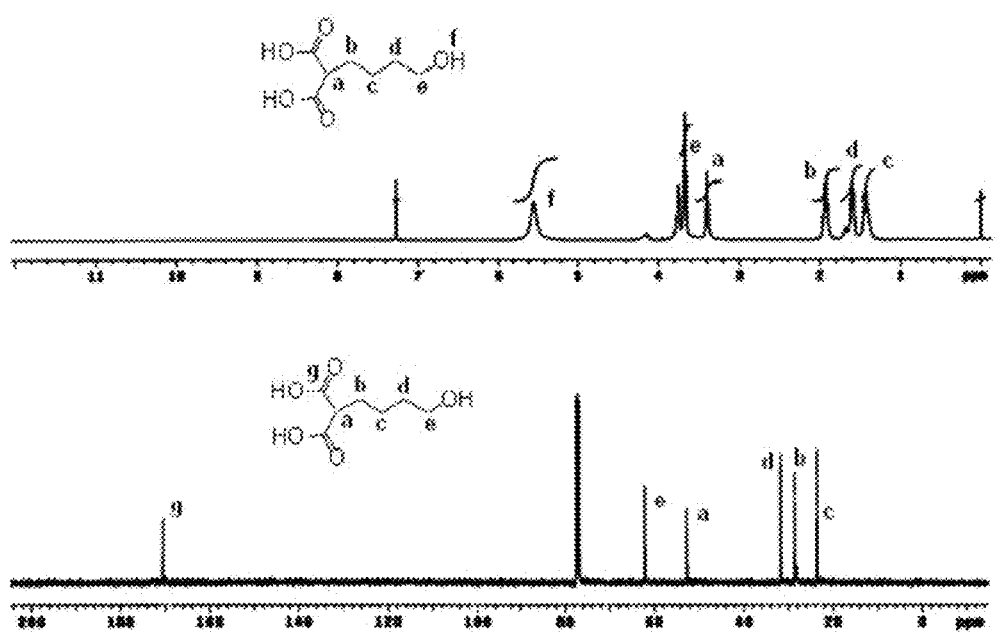
FIG. 7 shows $^1$H and $^{13}$C NMR spectra of the final AB2 monomer (4) using CDCl$_3$ as a solvent; absence of the ethyl ester protons and acetyl group in the NMR spectra confirms the hydrolysis of compound 3 and the formation of compound 4; all peaks are assigned to the corresponding protons and carbons, which confirm the presence of the expected product.
Figure 8:
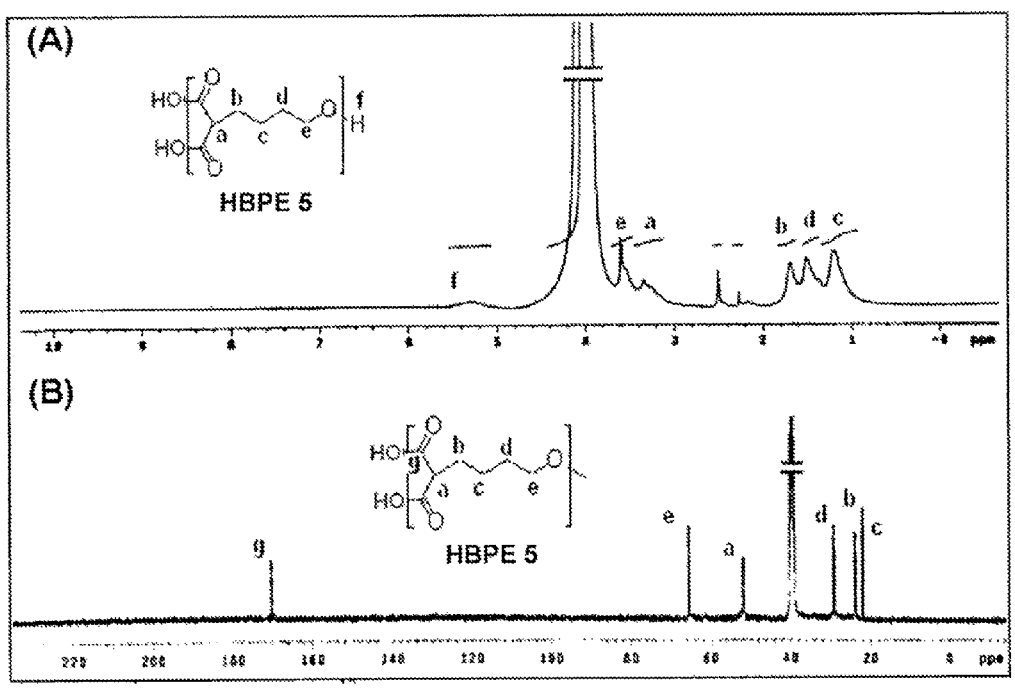
FIG. 8 shows $^1$H and $^{13}$C NMR spectra of amphiphilic hyperbranched polymer (5), confirming the preparation of high molecular weight polymer; the broadening of the sharp peaks in $^1$H NMR spectrum of the monomers also indicates the formation of polymer having a large number of chemically equivalent protons with same δ value.
Figure 9:
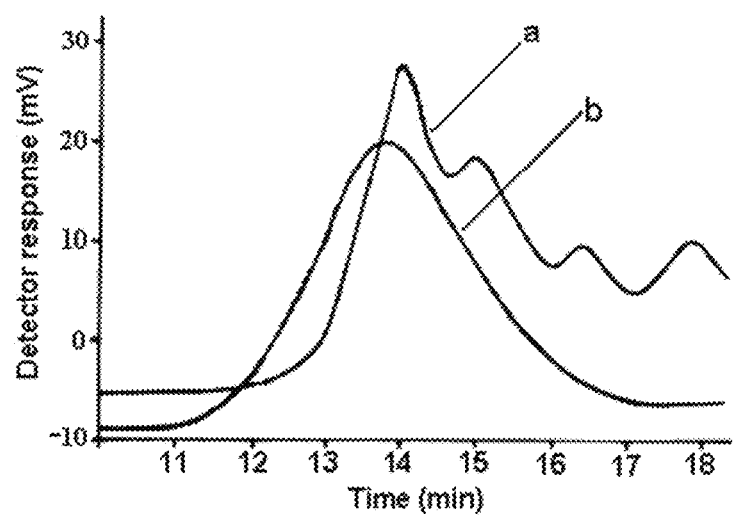
FIG. 9 provides GPC traces of polyester 5, polymerized at 150° C. at atmospheric pressure and under high vacuum; a) before applying vacuum, showing the presence of low molecular weight polymers and oligomers; b) high molecular weight polymer was formed after applying vacuum; for a comparative study between the average molecular weight (Mw) and the polymerization time at 150° C., the samples were taken from the reaction mixture periodically and analyzed by GPC; with increasing time there was an increase in the molecular weight, whereas a dramatic increase in the polymer's molecular weight was observed when high vacuum was applied; moreover, when the evacuation was continued for more than 2 h, the resulting polymers were found to be insoluble in all the solvents; the average molecular weight of polymer (5) was Mw=42,000, PD=1.6.
Figure 10:
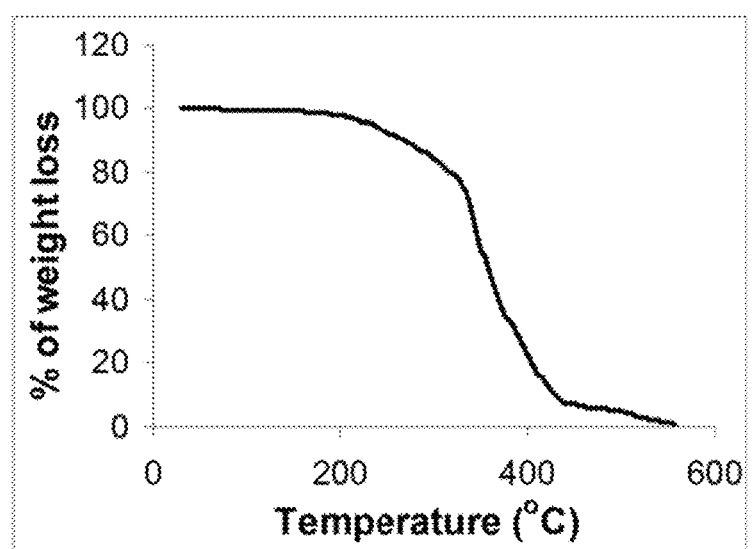
FIG. 10 is a TGA thermogram trace of polyester 5 at a heating rate of 10° C./min in air; the thermogram obtained is typical of an aliphatic hyperbranched biopolymer; the hyperbranched polymer exhibits a moderate thermal stability; thermal decomposition of the polymer was initiated at ~210° C.; at 225° C., the polymer has only lost about 2.5% of its weight, mainly due to evaporation of the volatile compounds (such as H2O, CHCl3 and DMF), before the induction of its thermal degradation; approximately a 10% weight loss occurred at 250° C.

The amphiphilic hyperbranched polyester (HBPE 5) was rationally designed for the development of theranostic PNPs (nanoparticles providing both a therapeutic agent and a diagnostic modality), by employing strategies of nanoparticle formation and drug/dye encapsulation in one process. FIG. 1-2 shows our synthetic strategy, leading to the formation of a novel, water soluble, $AB_2$ monomer 4 which upon polymerization gives rise to the water insoluble, biodegradable polymer 5, capable of encapsulating dyes/drugs for therapeutic applications. The melt polymerization technique was followed for the polymer synthesis, where we observed that at the initial stages of polymerization, oligomers and low molecular weight polymers were obtained. However, upon applying vacuum, a high molecular weight polymer ($M_w$=42,000, PD=1.6) was formed (FIG. 9). The resulting polyester was highly branched, having carboxylic acid groups at the surface and obtaining a three dimensional architecture with hydrophobic cavity. Hence contrary to conventional linear polyesters, our branched polymer is amorphous, amphiphilic, soluble, highly surface functional, biodegradable and has a cavity for effective encapsulation of guest molecules, which suggest its versatility in biomedical applications. Through thermal gravimetric analysis (TGA), we determined that the polymer exhibits moderate thermal stability (10% weight loss at 250° C. in air), which is typical for a biodegradable polymer (FIG. 10). The polymer was further characterized using spectroscopic and chromatographic techniques (FIG. 5-8). Subsequently, the presence of free carboxylic acid groups at the surface prompted the generation of a library of functional polymers using carbodiimide chemistry. We used 1,1'-carbonyldiimidazole (CDI), as a water insoluble carbodiimide, and either ethylenediamine or propargylamine for the synthesis of surface-aminated cationic polymer (HBPE-EDA 6) and clickable polymer, respectively (HBPE-PA 9, FIG. 3). Hence, the former surface-aminated polymer may be a good candidate for non-specific cell internalization, whereas, the later one might be a platform for targeted therapy due to the facile conjugation of specific cellular receptor ligands, such as folic acid, via click chemistry (FIG. 4).

Polymeric Nanoparticle (PNP) Synthesis and Drug/Dye Encapsulation

Figure 20:
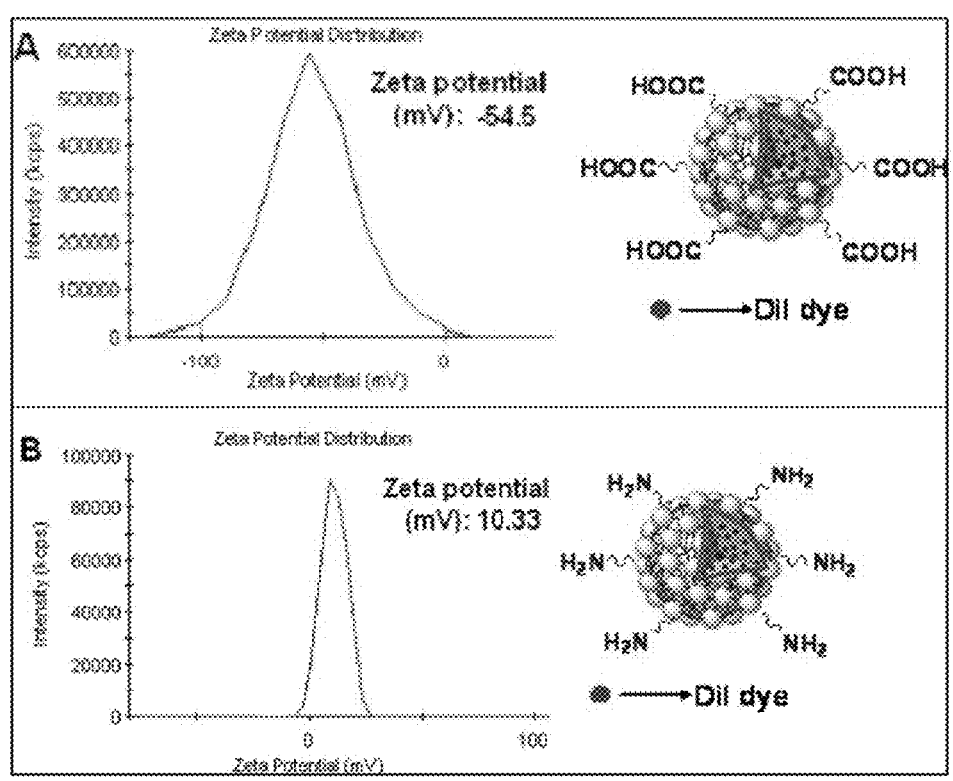
FIG. 20 shows the electrokinetic potential (zeta potential) of the synthesized polymeric nanoparticles; the zeta potential of the non-aminated polymeric nanoparticles is negative (A, ζ=−54.5 mV), as expected, due to the presence of surface carboxylic acid groups; not surprisingly, the zeta potential of the aminated polymeric nanoparticles is positive (B, ζ=10.33 mV), where the low positive value indicates the partial amination of the nanoparticles with the presence of less number of free carboxylic groups than amine groups at the surface.

In order to prepare functional PNPs, a modified solvent diffusion method was used, where the nanoparticle formation and guest molecule encapsulation in the hydrophobic cavity took place in one-pot. The amphiphilic polymer and hydrophobic guests were dissolved in anhydrous dimethylformamide (DMF) and added drop-wise to water under continuous stirring, driving both the self-assembly and encapsulation processes and resulting in the synthesis of functional PNPs. The resulting PNPs were highly stable in aqueous buffered solution for more than a year, without significant reduction in the fluorescent emission of the encapsulated dyes and can be concentrated without significant precipitation. Therefore, near infra red dye (DiI, DiR and DiD) encapsulated PNPs (8a-c and 9a-c) were synthesized from the corresponding carboxylated and aminated polymers (HBPE 5 and HBPE-EDA 6, respectively). Alternatively, the aminated PNPs (9a-c) can be prepared from the carboxylated PNPs (8a-c) using water soluble carbodiimide, EDC, [1-ethyl-3-(3-dimethylaminopropyl) carbodiimide hydrochloride] and ethylenediamine (FIG. 3). Amination of these nanoparticles was confirmed by an overall surface charge (ζ-potential) measurement, where a positive surface potential was obtained in the case of aminated PNPs (FIG. 20). Propargylated PNPs were also synthesized with DiI dye (10a), DiR dye (10b), DiD (10c), DiI with the anti-cancer drug paclitaxel (10d) and with AzT (10e) using the above strategy. These PNPs (10a-e) are very important synthon for the synthesis of a library of functional PNPs via click chemistry. To demonstrate the applicability of click chemistry in this system, the alkyne-azide click was engineered to occur at the interface between the propargylated carboxylic acid corona of the PNPs and the aqueous phase in which the azide-functionalized folic acid is dissolved. Therefore, folate-decorated PNPs (11a-e) were prepared using this 1,3-dipolar cycloaddition reaction, click chemistry, mediating the targeted drug delivery to cancer cells that overexpress the folate receptor (FIG. 4).

Polymeric Nanoparticle Characterization

Figure 11:
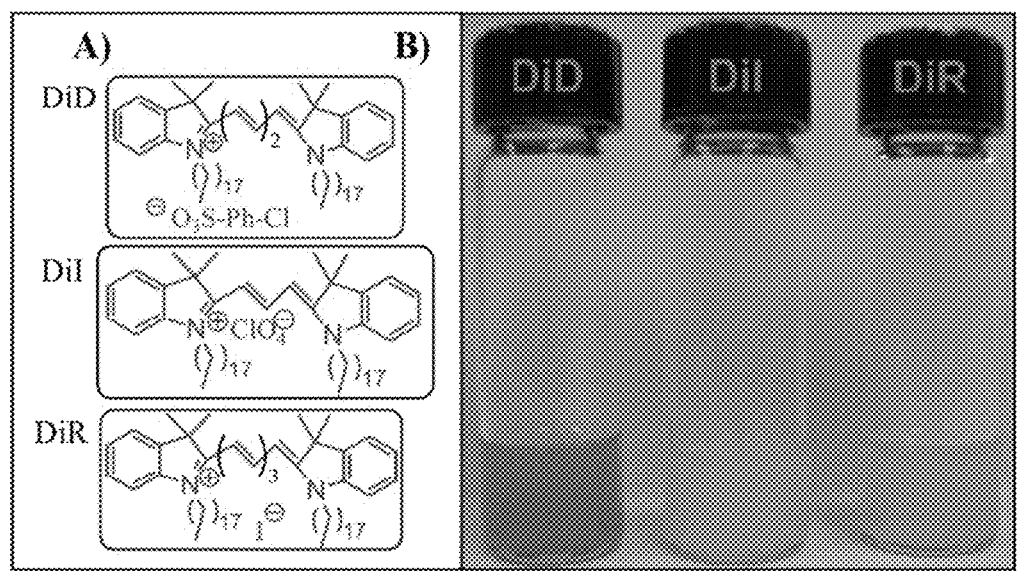
FIG. 11 shows in A) the chemical structure of DiD, DiI and DiR; these dyes are water insoluble in nature and are primarily used to visualize cell membranes; and in B) a photographic image showing an aqueous (PBS) suspension of HBPE nanoparticles encapsulating the corresponding dyes (8a-c); similarly, one can encapsulate a hydrophobic drug or a combination of drug and dye; highly dispersed dyes/drugs encapsulated polymeric nanoparticles are stable in wide range of solvents under physiological conditions. The fluorescence of the resulting dye-encapsulated polymeric nanoparticles is bright and is not accompanied by any significant quenching upon encapsulation of photobleaching upon prolonged imaging.
Figure 12:
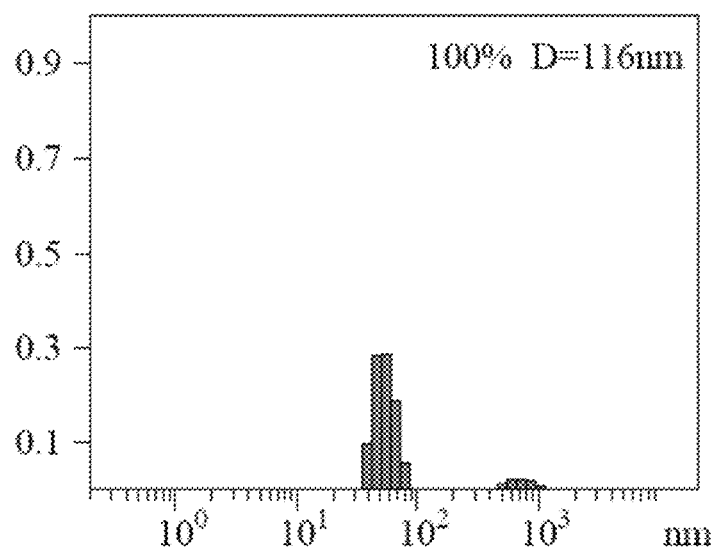
FIG. 12 shows the hydrodynamic diameters of the nanoparticles as measured by dynamic light scattering (DLS) instrument; measurement data shows the average hydrodynamic diameter of the particles are ranging between approximately 90±20 nm.
Figure 13:
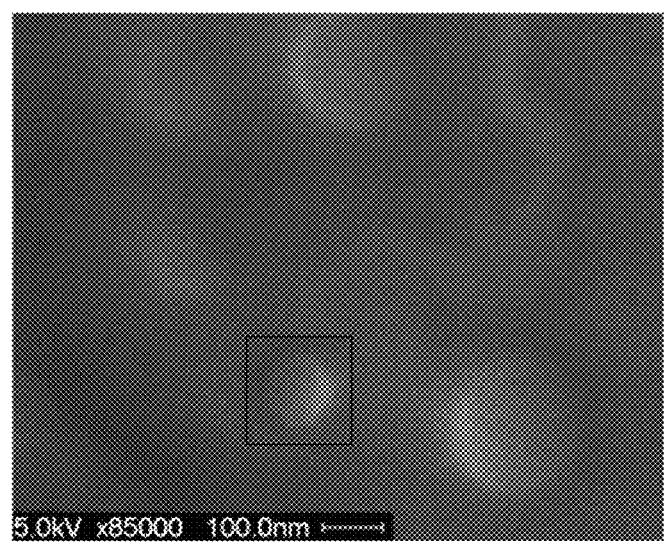
FIG. 13 presents Scanning Electron Microscope (SEM) images of the polymeric nanoparticles showing an average diameter ranging from 115±25 nm, in accordance with the DLS data shown in FIG. 12; remarkably, the black rectangular box in the image indicates that the nanoparticles are spherical in shape, as expected.
Figure 14:
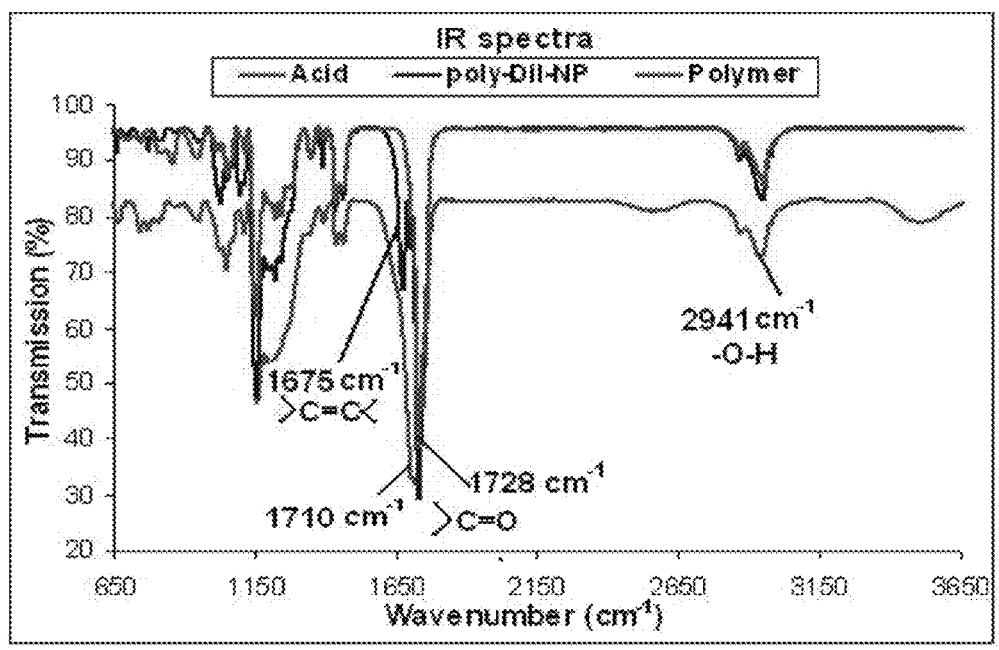
FIG. 14 depicts FT-IR spectra of the final monomer 4 (Acid), HBPE 5 (Polymer) and the dye encapsulating PNPs 8a, demonstrating presence of dye within the PNPs; the presence of a FT-IR band at 1728 cm$^{-1}$ for the ester group indicates the formation of the hyperbranched polyester from the monomer (band at 1710 cm$^{-1}$ for aliphatic carboxylic acid group); the band at 1675 cm$^{-1}$ is attributed to a conjugated alkene group, confirming the encapsulation of the dye inside a hydrophobic cavity of the PNPs.
Figure 15:
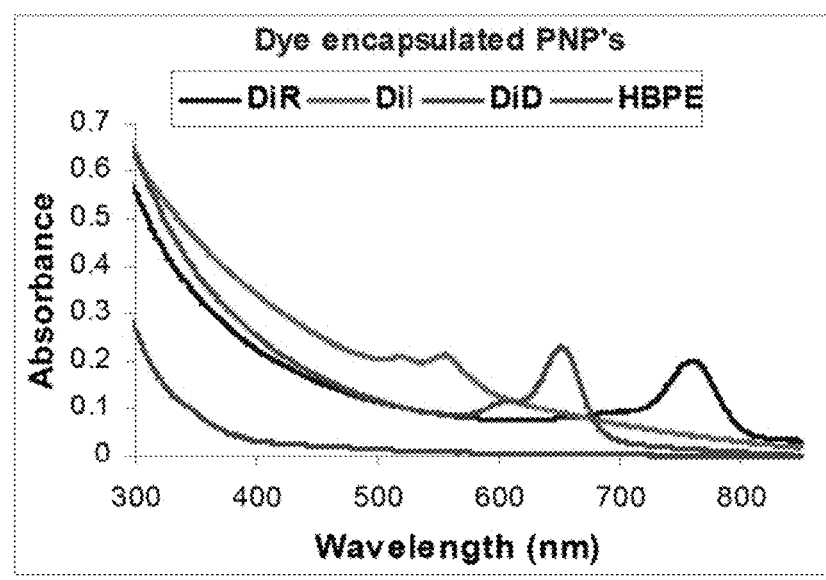
FIG. 15 are UV/Vis spectra of the dye (DiI, DiD, DiR)-encapsulating PNPs (8a-c), showing the presence of the NIR dyes with absorption maxima at 552, 650 and 755 nm, respectively.
Figure 16:
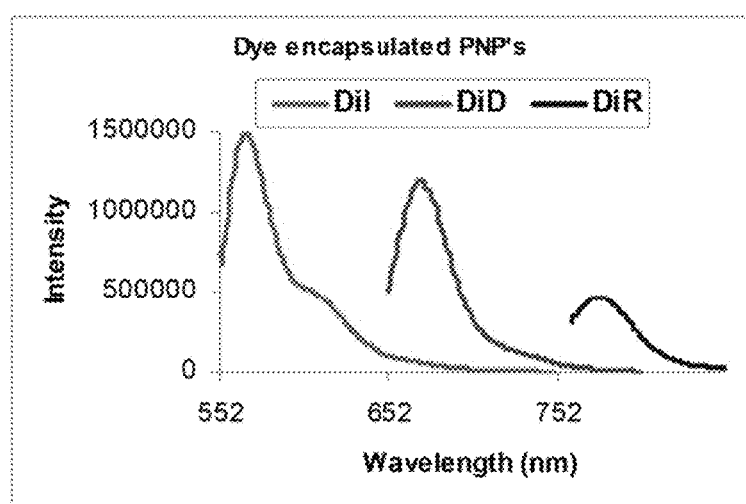
FIG. 16 shows the characteristic fluorescence emission spectra of dye encapsulating polymeric nanoparticles (8a-c) in DI water; the fluorescence intensity maxima of these nanoparticle solutions at 570 nm, 675 nm and 780 nm indicate the presence of NIR dyes DiI, DiD and DiR, respectively, in the hydrophobic domain of the polymeric nanoparticles; no changes in fluorescence intensity or quenching of the dyes was observed upon encapsulation and subsequent storage of the nanoparticles at 4° C. for months, demonstrating the high fluorescence stability of these dye encapsulated polymeric nanoparticles; note the multiple imaging capability using 3 different wavelengths.
Figure 17:
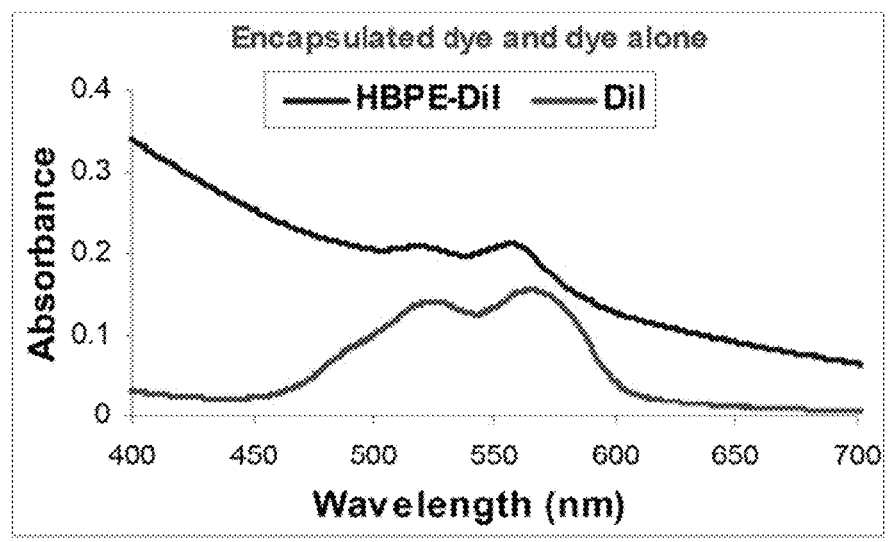
FIG. 17 are UV/Vis spectra of the DiI dye encapsulating PNPs (8a) and the dye alone; a blue shift (by 10 nm) was observed in the UV/Vis absorption maxima in the case of DiI encapsulating PNPs, which confirmed the presence of the dye within the hydrophobic domain of the PNPs.
Figure 18:
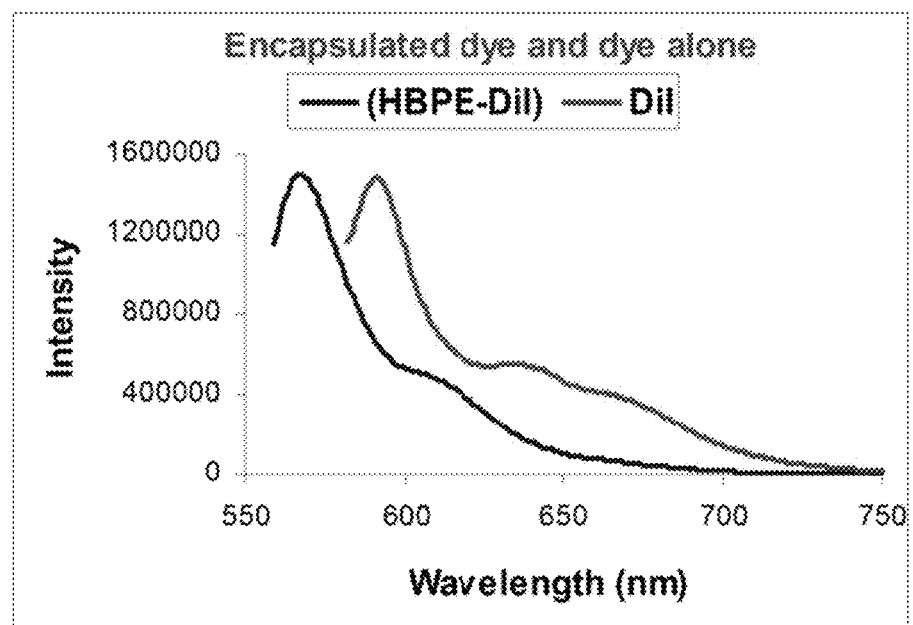
FIG. 18 depicts the blue shift (23 nm) in the fluorescence emission of DiI encapsulating HBPE nanoparticles (8a) as compared to free dye; this is due to both van-der Walls (hydrophobic) and electronic interactions of the dye with the polymeric cavity, confirming the presence of dye inside the polymer cavity.
Figure 19:
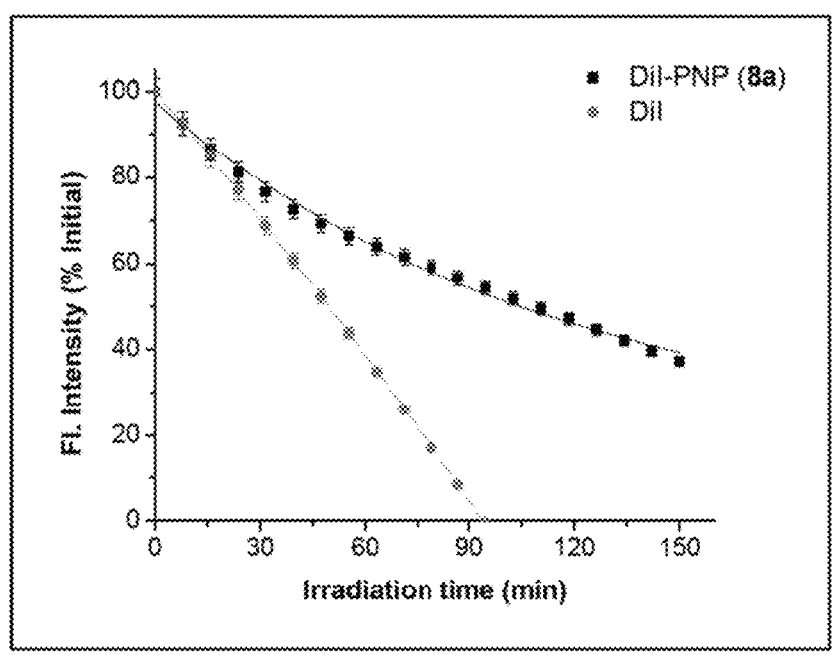
FIG. 19 shows a photo-stability study of the DiI encapsulating PNPs (8a) and DiI alone in solution in the presence of UV light, demonstrating the stability of the dye when encapsulated inside the polymeric cavity compared to the free dye.
Figure 22:
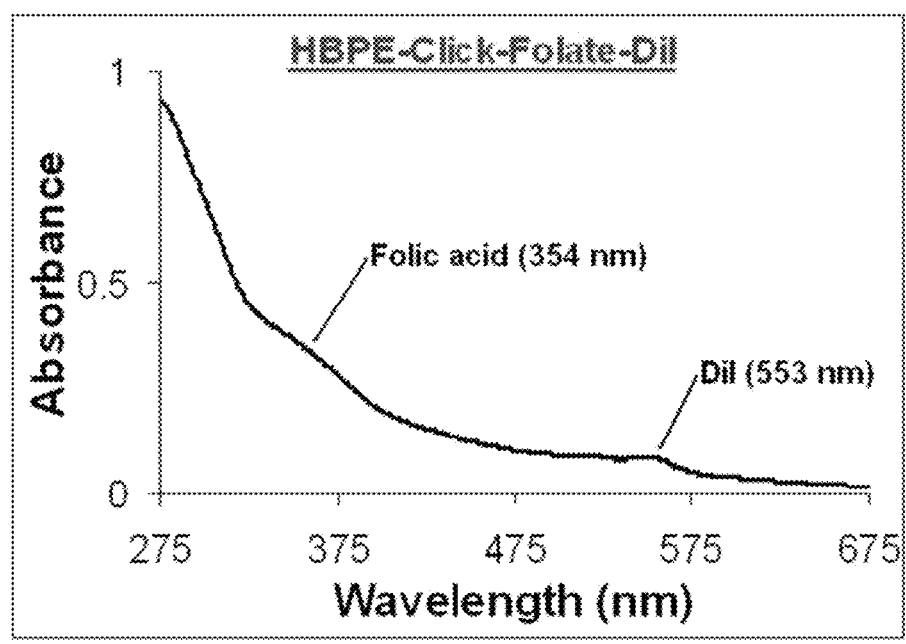
FIG. 22 is a UV/Vis spectrum of the folate-clicked, DiI-encapsulating PNPs 11a, showing the presence of both the encapsulated dye (553 nm) and surface clicked with folate (354 nm); similar results were obtained for the paclitaxel- and DiI-encapsulating PNPs 11d, prepared for targeted cancer therapy.
Figure 23:
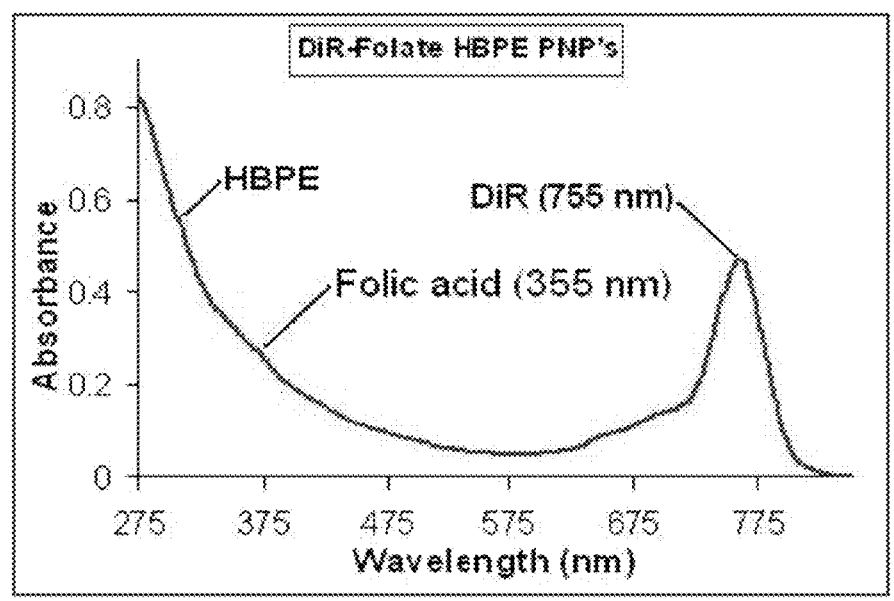
FIG. 23 shows an UV/Vis spectrum of the folate-clicked, DiR-encapsulating PNPs 11b, showing the presence of both the encapsulated DiR (755 nm) and surface clicked with folate (355 nm)

The approximate hydrodynamic diameter of the PNPs was determined though Dynamic Light Scattering (DLS), ranging from 100±20 nm, which was similar to that of the unmodified nanoparticles (FIG. 12). Well-formed spherical PNPs were observed by scanning electron microscopy (SEM, FIG. 13) and the average diameter of these PNPs was 115±25 nm, demonstrating a direct correlation with the DLS data. Remarkably, the black rectangular box in the SEM image indicates that the shape of the nanoparticles was spherical as expected from the structure of the original polymer HBPE 5. The formation of hydrophobic microdomains and the encapsulation of NIR dyes inside the PNPs were confirmed by fluorescence measurement of free DiI dye and encapsulated DiI in PNPs (8a, FIG. 18). In this experiment, DiI dye was dissolved in DMF and allowed to evaporate at room temperature and then dispersed in water. A blue shift (by 23 nm) was observed in the fluorescence emission of DiI-encapsulated HBPE nanoparticles (570 nm) as compared to the free non-encapsulated DiI dye (593 nm) in water. This indicated the presence of the dye inside the electronic environment of the polymer's cavity, confirming the presence of hydrophobic microdomains in the PNPs. Similar results were obtained from UV/Visible spectroscopy studies, where a blue shift was observed for the encapsulated DiI (FIG. 17), further confirming the entrapment of the dye inside the cavity. Interesting results were obtained from Fourier Transform Infra Red (FT-IR) spectroscopy (FIG. 14), and these corroborated the formation of PNPs encapsulating the DiI dye. The presence of the aliphatic alkenes' characteristic band at 1675 cm$^{-1}$ indicated the encapsulation of DiI via conjugated double bonds inside the nanoparticle cavity. Subsequently, we prepared three different dye (DiI, DiR and DiD) containing PNPs (8a, 8b and 8c, respectively) from the polymer 5 as shown in FIG. 3 and FIG. 15. Characteristic fluorescence emission spectra of the dye-loaded PNPs in PBS buffer are shown in FIG. 16. The fluorescence intensity maxima of these nanoparticles were at 570, 675 and 780 nm, indicating the presence of the NIR dyes DiI, DiD and DiR, respectively, within the hydrophobic domain of the PNPs. These functional fluorophore-containing PNPs were highly stable in aqueous solution (FIG. 11). Next, NIR dye and paclitaxel co-encapsulated folate-clicked PNPs (11a-e) were characterized by UV/Vis spectroscopy (FIG. 22-23).

In Vitro Cytotoxicity

Figure 24:
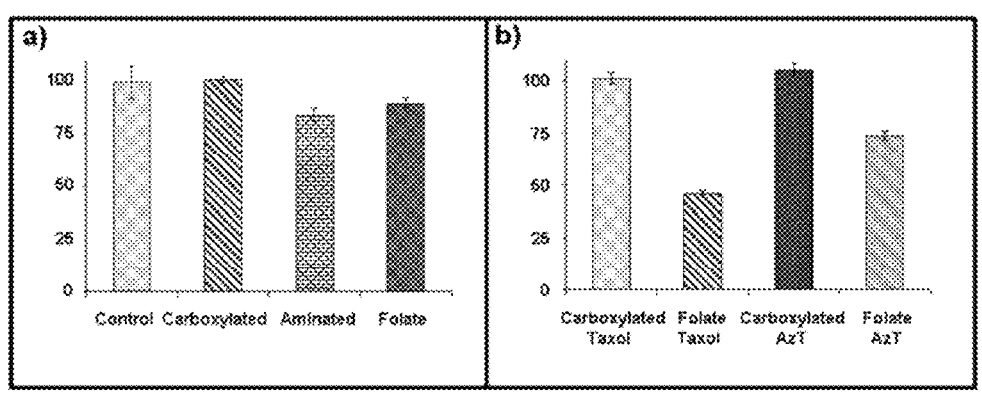
FIG. 24 shows bar graphs acknowledging the potential biomedical applications of the synthesized PNPs; we evaluated their cytotoxicity, through the MTT assay; first, we examined the potential in vitro differential cytotoxicity of carboxylated, aminated, and folate-decorated DiI-containing PNPs, using a lung carcinoma (A549) cell line; results indicated that the carboxylated and folate-conjugated PNPs exhibited nominal cellular cytotoxicity (less than 4% compared to the control), whereas the aminated PNPs induced cell death to approximately 10% of the cell population (FIG. 24a); indeed, the folate-decorated DiI and paclitaxel co-encapsulating PNPs (11d) induced a significant reduction in cell viability, as more than 50% of the cell population underwent cell death (FIG. 24b); furthermore, as most lung carcinomas exhibit aberrant telomerase activity, leading to cell immortality, we encapsulated the reverse transcriptase inhibitor AzT in PNPs (11e); we found that folate-decorated DiI and AzT co-encapsulating PNPs induced significant cell death, as previously reported in literature via inhibition of telomerase activity (FIG. 2b); overall, these data suggest that the induction of cell death is mainly mediated by either paclitaxel or AzT, and not by the fluorophores; control cells were treated with 1×PBS; average values of four measurements are depicted±standard error.

Having in mind the potential biomedical applications of the synthesized PNPs, we evaluated their cytotoxicity, through the MTT assay. First, we examined the potential in vitro differential cytotoxicity of carboxylated, aminated, and folate-decorated DiI-containing PNPs, using a lung carcinoma (A549) cell line. Results indicated that the carboxylated and folate-conjugated PNPs exhibited nominal cellular cytotoxicity (less than 4% compared to the control), whereas the aminated PNPs induced cell death to approximately 10% of the cell population (FIG. 24a). Considering these findings, the potential use of these PNPs in imaging and drug delivery applications, either in vitro or in vivo, is anticipated. Hence, we examined if PNPs can be used for targeted drug delivery, by examining the cytotoxic efficacy of PNPs co-encapsulating DiI and the hydrophobic chemotherapeutic agent paclitaxel. Indeed, the folate-decorated DiI and paclitaxel co-encapsulating PNPs induced a significant reduction in cell viability, as more than 50% of the cell population underwent cell death (FIG. 24b). Furthermore, as most lung carcinomas exhibit aberrant telomerase activity, leading to cell immortality, we encapsulated the reverse transcriptase inhibitor AzT in PNPs. We found that folate-decorated DiI and AzT co-encapsulating PNPs induced significant cell death, as previously reported in literature via inhibition of telomerase activity (FIG. 24b). Overall, these data suggest that the induction of cell death is mainly mediated by either paclitaxel or AzT, and not by the fluorophore. Specifically, the enhanced in vitro cytotoxicity of the folate-decorated DiI and paclitaxel co-encapsulating PNPs in A549 cells hints the successful targeting of carcinomas that overexpress the folate receptor on their plasma membrane. Furthermore, these results suggest that the co-encapsulation of a fluorophore and a therapeutic agent in our PNPs can be utilized for cellular targeting, such as in cancer or anti-HIV CD4$^+$-specific therapeutic regimes, visualization of the drug's homing and monitoring of tumor regression in clinical studies.

In Vitro Cellular Uptake of PNPs

Figure 21:
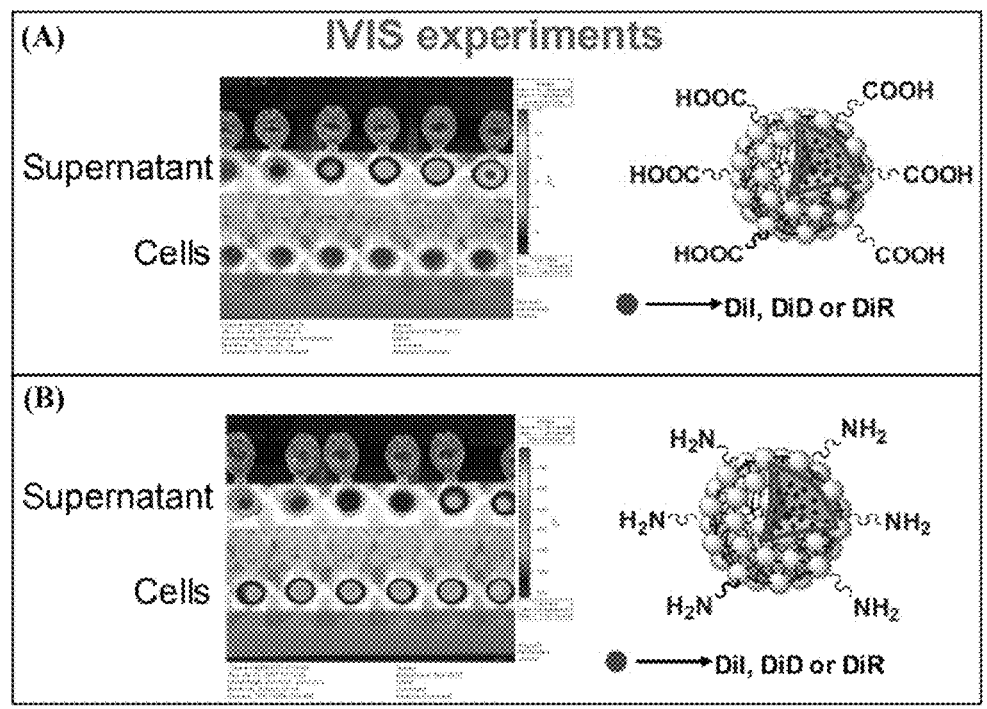
FIG. 21 presents cell internalization studies using Xenogen's IVIS 50; in these experiments either carboxylated (negative, 8b) or aminated (positive, 9b) nanoparticles were incubated with cells from the A549 lung cancer cell line; in these representative studies, near infrared DiR encapsulated nanoparticles were used, although similar results were observed with DiD and DiI; as expected, internalization was observed only when the positively charged aminated DiR nanoparticles were used, as judged by the near infrared fluorescence coming from the cell pellets on FIG. 21B; note that when carboxylated nanoparticles are used (FIG. 21A), the fluorescence remains in the supernatant; these results demonstrate that cationic nanoparticles are a better candidate for the cell internalization studies and for cell tracking studies. In addition, it shows the capability of imaging in the near infrared.
Figure 25:
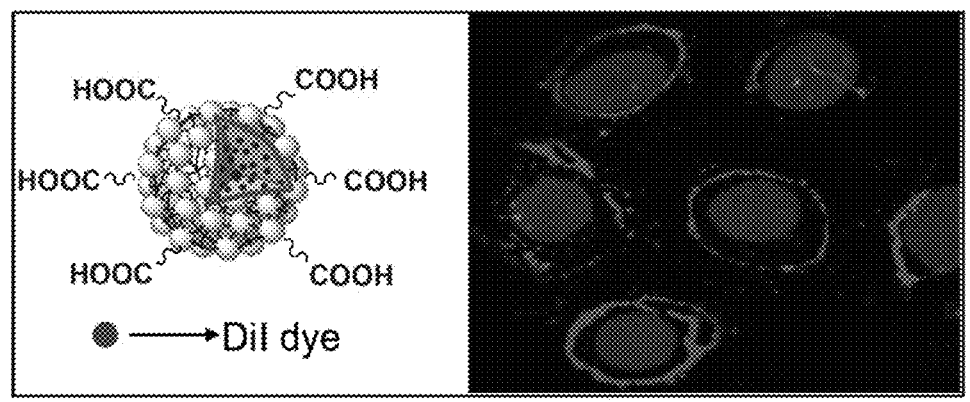
FIG. 25 shows a confocal laser-scanning microscopic image of A549 lung cancer cells incubated with DiI dye-encapsulated carboxylated polymeric nanoparticles (8a); dye encapsulated nanoparticles are incubated with the cells for 6 h; result shows no internalization of the nanoparticles into the cytoplasm, which demonstrates that the anionic (carboxylic groups at surface) polymeric nanoparticles are not the appropriate candidate for cell internalizations; instead, only cell membrane stained with the dye (outer red lines); the nucleus stained with DAPI (blue color)
Figure 26:
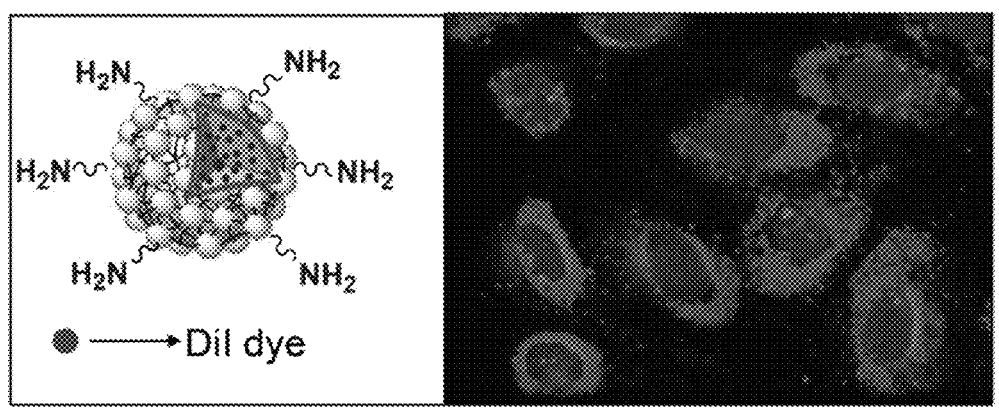
FIG. 26 shows a confocal laser-scanning microscopic image of A549 lung cancer cells incubated with DiI dye encapsulated aminated polymeric nanoparticles (9a); internalization of the nanoparticles into the cell cytoplasm was observed, which demonstrates that the cationic (amine groups at surface) polymeric nanoparticles are the appropriate candidate for cell internalizations; the nucleus stained with DAPI (blue color)

To demonstrate the capability of our functional PNPs to be internalized by cells and eventually exert specific intracellular activity, various preparations of PNPs were incubated with lung carcinoma cells (A549) for 6 h. Confocal images showed there was no internalization of the non-aminated PNPs, but only the cell membranes were found to be stained with the red DiI dye (outer red lines, FIG. 25). This demonstrates the proof-of-concept that the anionic (carboxylic groups at surface) PNPs are not appropriate candidates for cell internalization. To further corroborate this concept, we used A549 cells treated with aminated PNPs encapsulating DiI (9a). Contrary to the carboxylated PNPs, there was strong internalization of the cationic surface PNPs (FIG. 26). Notably, these PNPs did not affect cellular integrity and nuclear stability, failing to trigger apoptosis, even after 12 h of incubation. Hence, these results strongly support the notion that cationic (surface amine groups) PNPs are better vehicles for cell internalization. Subsequently, we performed in vitro cellular uptake studies, utilizing a Xenogen IVIS system. Similar results to the confocal studies were obtained. Specifically, aminated PNPs were found intracellularly, as fluorescent emission was recorded from the cell pellet. On the other hand, there was absence of fluorescence emission from the pellet of cells treated with non-aminated PNPs, suggesting lack of PNP internalization (FIG. 21, IVIS images). Similar results were obtained from other synthesized PNPs (8b-c and 9b-c) through the IVIS setup, in line with the confocal microscopy observations.

Figure 27:
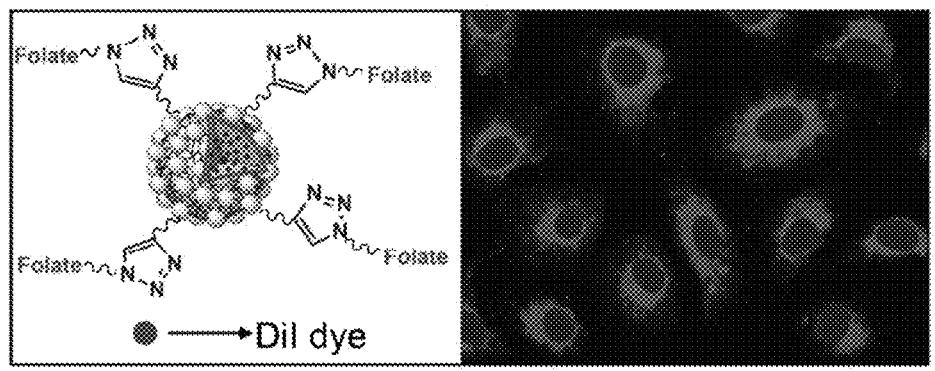
FIG. 27 depicts a confocal laser-scanning microscopic image of A549 lung cancer cells incubated with DiI dye encapsulated folate-immobilized polymeric nanoparticles (11a); the particles were incubated with the cells for 6 h.; internalization of the nanoparticles into the cell was observed, demonstrating the presence of folate receptor in the A549 cancer cells and therefore inducing a folate-receptor mediated internalization.
Figure 28:
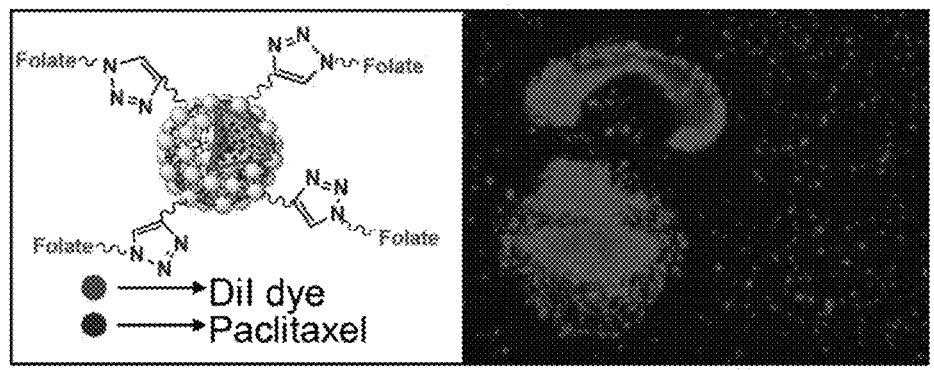
FIG. 28 provides a confocal laser-scanning microscopic image of A549 lung cancer cells incubated with folate modified nanoparticles (11d) encapsulating both a hydrophobic dye (DiI) and a hydrophobic anti-cancer drug (paclitaxel); the nanoparticles were incubated with the cells for 6 h. Neither the fluorescence intensity of the dye, nor the cytotoxic effects of the anti-cancer drug are affected when encapsulated in the polymeric nanoparticle; experiments show that paclitaxel-induced mitotic arrest results in apoptotic cell death of lung carcinoma cells (A549)
Figure 29:
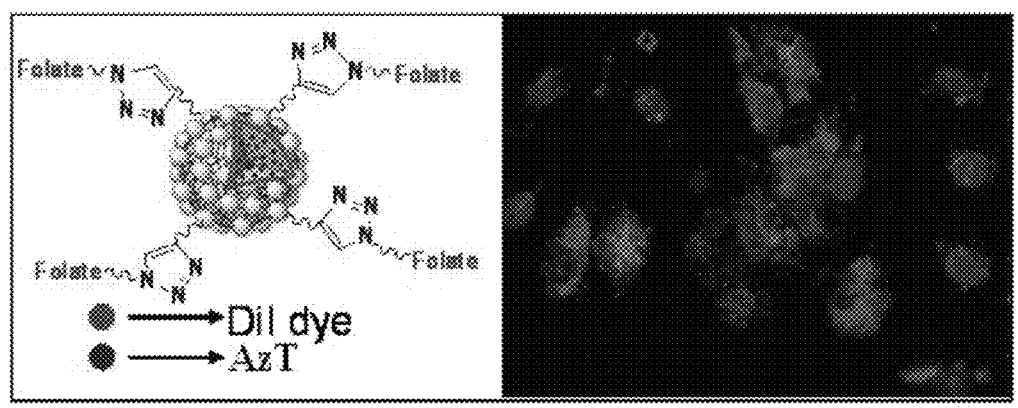
FIG. 29 is a confocal laser-scanning microscopic image of A549 lung cancer cells incubated with folate modified nanoparticles (11e) encapsulating both a hydrophobic dye (DiI) and a hydrophobic anti-HIV drug (AzT); the nanoparticles were incubated with the cells for 6 h; these experiments show that AzT-induced mitotic arrest results in apoptotic cell death of lung carcinoma cells (A549)

Then, we investigated the targeting potential of our PNPs and cellular uptake of the folate-clicked PNPs (11a), comparing these PNPs with the corresponding carboxylated ones (8a). Confocal microscopy revealed the effective uptake of the folate-functionalized PNPs by A549 cells (FIG. 27), in contrast to the carboxylated ones (FIG. 25). The enhanced cellular uptake of the folate-decorated PNPs may be attributed to folate-receptor mediated internalization. Accordingly, through confocal studies, we observed that the efficiency of folate-decorated PNPs uptake significantly improved upon increasing the incubation time, while no cytotoxic effects were observed via the MTT assay. Hence, the enhanced time-dependent uptake and retention of these PNPs is likely due to folate-receptor recycling, which is typical of constitutive nutrient receptor endocytic trafficking. Subsequently, to demonstrate the folate-clicked PNPs' (11a) proof-of-concept theranostic capability towards cancer cells, we used DiI and paclitaxel co-encapsulating PNPs (10d). Then, the surface propargyl groups were clicked with azide-functionalized folic acid, in order to achieve targeted drug delivery with optical imaging capability for spatiotemporal monitoring. Lung carcinoma cells overexpressing the folate receptor were treated with these PNPs (11d). After a 3 h-long incubation, confocal microscopic examination revealed cellular internalization and induction of paclitaxel-mediated mitotic arrest (FIG. 28), in accordance to the literature. This illustrates that paclitaxel's therapeutic efficacy was preserved, despite its PNP encapsulation. Furthermore, treatment with paclitaxel-containing PNPs triggered dramatic cellular morphological changes after 12 h of incubation, leading to cell death. Furthermore, as most lung carcinomas exhibit aberrant telomerase activity, leading to cell immortality, we encapsulated the reverse transcriptase inhibitor AzT in PNPs. We found that folate-decorated DiI and AzT co-encapsulating PNPs induced significant cell death, as previously reported in literature via inhibition of telomerase activity (FIG. 29). These observations strongly support the importance of encapsulating this potent anti-tumor agent within the polymeric cavity and targeting its delivery, in order to prevent damaging non-transformed cells and healthy tissue. Taken together, these findings support the principle that folate-decorated PNPs can target and deliver chemotherapeutic agents to folate-receptor-overexpressing carcinomas, while visualizing the drug's homing. Thus by modifying the targeting moiety at the theranostic PNPs' surface, other carcinomas or ailing cells may be targeted tailoring the therapeutic regime, while obtaining important spatiotemporal information for clinical decision making.

Flow Cytometric Assessment of PNPs Uptake

Figure 30:
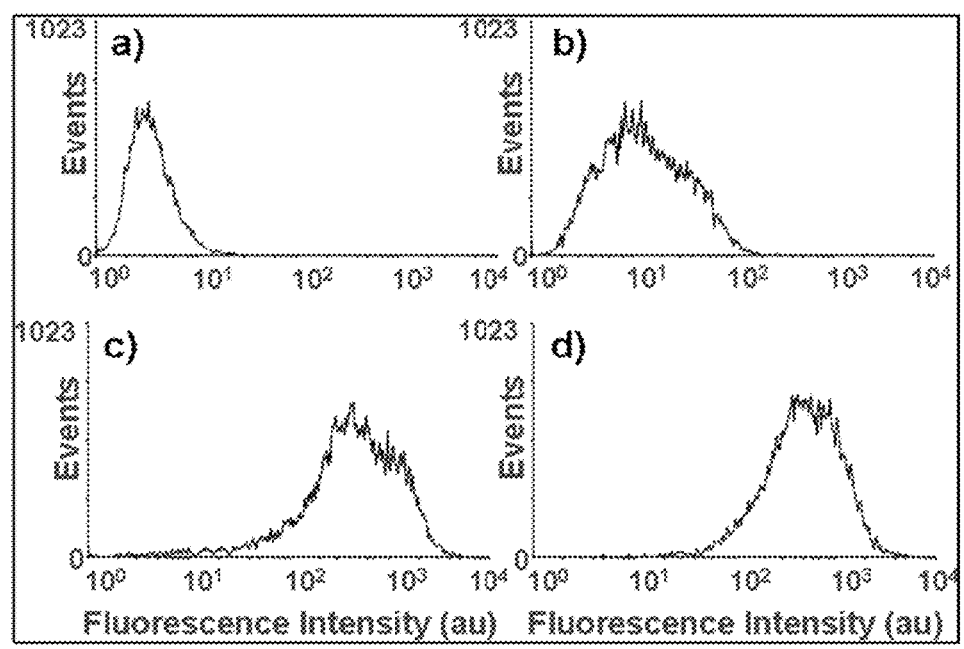
FIG. 30 provides an assessment of the PNP-cell association via flow cytometry, where in a) absence of fluorescence emission is observed in control mock-treated cells (1×PBS), in b) partial association of the dye-loaded non-aminated PNPs (8a) is observed, in c) aminated (9a) and d) folate-decorated (11a) nanoparticles interact more profoundly with the cells, as indicated by higher levels of fluorescence emission.

To corroborate the PNPs cellular uptake ability, a detailed flow cytometry analysis was performed with functional PNPs (8a, 9a and 11a) and A549 cells. Specifically, through flow cytometry, we determined the DiI-derived cell-associated fluorescence emission in a quantifiable fashion. As shown in FIG. 30b, limited fluorescence emission was observed from cells treated with the carboxylated PNPs (8a). This indicated nominal cell association of these carboxylated PNPs (8a), when compared to the control non-treated cells (FIG. 30a) where there was lack of fluorescence emission. This is in accordance with the data from the confocal and IVIS studies, confirming the observation that the anionic surface of the nanoparticles interacts with the cell's plasma membrane. Contrary to this and similar to the confocal microscopic observations, cells incubated with aminated PNPs (9a) showed three-fold higher fluorescence emission and binding activity when compared to the control mock-treated cells, as shown in FIG. 30c. Similar to other cationic small molecules and peptides, the interaction of the surface-localized positive charge of the aminated PNPs with the negatively charged cell membrane facilitated the association of the PNPs with the cell membrane at the extracellular milieu and the subsequent cellular uptake and retention, as observed through previously discussed in vitro studies. Interestingly, upon clicking the carboxylated PNPs with folic acid, a higher cell-associated fluorescence emission was observed (FIG. 30d). Notably, the profound cellular uptake of the folate-decorated PNPs (11a), being comparable to the aminated ones, is attributed to the specific folate-receptor-mediated internalization and intracellular retaining. Overall this indicates that the specific targeting of PNPs through targeting moieties, such as folate, is feasible and equally efficient as the non-specific electrostatic-mediated uptake of cationic entities, rendering targeted PNPs useful for potential in vivo applications.

Drug/Dye Release Study of Functional PNPs

Figure 31:
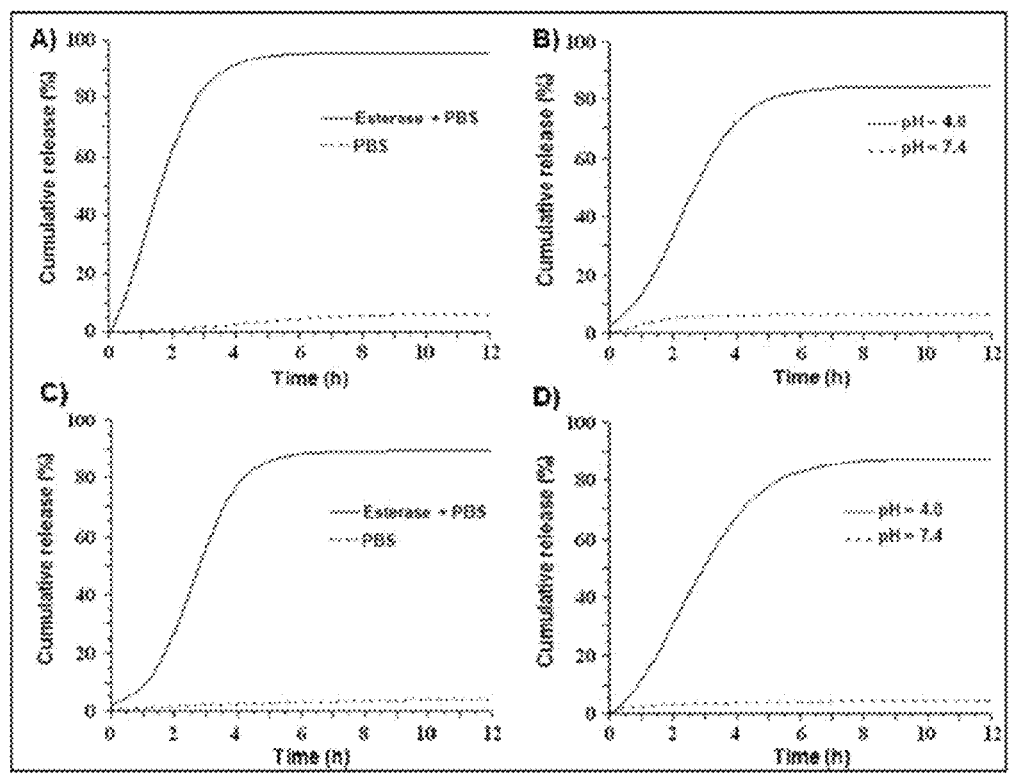
FIG. 31 shows drug (paclitaxel) and dye (DiI) release profiles of functional PNPs (11d) in PBS (pH=7.4) at 37° C.; release of paclitaxel (A & B) and DiI (C & D) were observed in the presence of an esterase enzyme (A & C) and at pH 4.0 (B & D); these results indicate that the PNPs are degradable in the presence of an esterase enzyme and at low pH; a controlled release of drug and dye was observed.

The therapeutic application of our polymeric nanoparticles is influenced by the rate of release of the encapsulated drug from the polymeric cavity. To evaluate 11d's drug release profile, enzymatic (esterase) and low-pH degradation experiments were performed. Results indicate a fast release of the drug (paclitaxel) from the nanoparticle 11d upon esterase incubation, reaching a plateau within 4 hours (FIG. 31A). A similar release profile of the drug was observed at pH 4.0, reaching a plateau within 4.5 hours (FIG. 31B). No significant release of the drug was observed from nanoparticles incubated in PBS, pH 7.4. These results demonstrate the stability of the polymeric nanoparticles during storage (PBS), and their cargo release only after cellular uptake via either esterase-mediated degradation or in acidified lysosomes. Only after folate-receptor-mediated uptake did the PNPs 11d become cytotoxic upon intracellular release of the therapeutic agent. Interestingly, even slower release of the dye was observed, both upon esterase incubation and at pH 4.0 (FIGS. 31C and 31D). However, no release of the dye was observed at normal physiological pH (7.4). The observed differential release of the drug vs. the dye from PNPs 11d may be attributed to the drug's (paclitaxel) size and hydrophobic nature.

Experimental Section

Materials

Anhydrous DMF, DMSO, 3-(4,5-Dimethylthiazol-2-yl)-2, 5-diphenyltetrazolium bromide (MTT), 1,1'-Carbonyldiimidazole (CDI), N-hydroxysuccinimide (NHS), AZT (azidothymidine), diethylmalonate and other chemicals were purchased from Sigma-Aldrich and used without further purification. Near Infra Red dyes (DiI-D282, DiD-D7757, and DiR-D12731) and 4', 6-diamidino-2-phenylindole (DAPI-D1306) were purchased from Invitrogen, whereas the EDC (1-Ethyl-3-[3-dimethylaminopropyl]carbodiimide hydrochloride) was obtained from Pierce Biotechnology. The folate-receptor-overexpressing human lung carcinoma cell line A549 (CCL-185) was obtained from ATCC. Dialysis membranes were obtained from Spectrum Laboratories. Acetonitrile, tetrahydrofuran and other solvents were purchased from Fisher Scientific and used as received, unless otherwise stated.

Instrumentation

Infrared spectra were recorded on a PerkinElmer Spectrum 100 FT-IR spectrometer. UV/Vis spectra were recorded using CARY 300 BiO UV/Vis spectrophotometer. Fluorescence spectra were recorded on a NanoLog Horiba jobin Yvon fluorescence spectrophotometer. NMR spectra were recorded on a MERCURY 300 MHz spectrometer using the TMS/solvent signal as an internal reference. Gel permeation chromatography (GPC) results were obtained using JASCO MD 2010 Plus instrument with PD 2020 light scattering Precision Detector. Thermo gravimetric analyses (TGA) were performed on a SETARAM, Mettler TC11 instrument with sample sizes 10-20 mg. All the experiments were done using a heating rate of 10° C./min in air. Atomic Force Microscopic (AFM) images were obtained from Dimension 3100 Atomic Force Microscope from Veeco Digital Instruments. Confocal images were taken on a Zeiss Axioskop 2 mot plus confocal microscope. Flow Cytometry experiments were performed using a BD FACS Calibur multipurpose flow cytometer system from BD Biosciences. MTT study has been done using BIO-TEK Synergy HT multi-detection microplate reader. Dynamic light scattering (DLS) studies were done using a PDDLS/CoolBatch 40T instrument using Precision Deconvolve 32 software and SEM images were taken using Jeol 6400F scanning electron microscope. IVIS experiments were done using IVIS 50 imaging system from Xenogen imaging technologies. Analytical Thin Layer Chromatography (TLC) was performed on glass plates coated with silica gel GF 254 and are visualized in iodine vapor. Column chromatography was performed using silica gel (100-200 mesh) and the eluant is mentioned in the procedures below for each case.

Methods

Synthesis of 4-bromobutyl acetate (2)

Tetrahydrofuran (12.2 mL, 148.4 mmol) and potassium bromide (21.1 g, 176.5 mmol) were added in a 250 mL round bottom flask containing 150 mL acetonitrile. The reaction mixture was cooled to 0° C., followed by drop-wise addition of acetyl chloride (11 mL, 155.1 mmol). Subsequently, the mixture was brought to room temperature, where it was continuously stirred for 36 h. The reaction mixture was poured in water and extracted with ethyl acetate. The organic layer was washed with water, dried over $Na_2SO_4$, and concentrated to obtain the pure product as a colorless liquid.

Yield: 24.3 g (85%). bp: >250° C. $^1$H NMR (300 MHz, $CDCl_3$, δ ppm, J Hz): 1.79 (m, 2H), 1.92 (m, 2H), 2.03 (s, 3H), 3.46 (t, 2H, J=7.6), 4.08 (t, 2H, J=6.7). $^{13}$C NMR (75 MHz, $CDCl_3$, δ ppm): 20.87, 27.36, 29.36, 33.03, 63.43, 170.95. IR ($CHCl_3$): 3038, 2926, 1352, 1243, 1052 cm$^{-1}$.

Synthesis of 2-(4-Acetoxy-butyl)-malonic acid diethyl ester (3)

Compound 3 was prepared by following a previously reported method.{Santra, 2004 #6} Briefly, diethyl malonate 1 (10 g, 62.5 mmol), 4-bromobutyl acetate 2 (15.84 g, 81.3 mmol) were placed in a round bottom flask containing acetonitrile (120 mL) and stirred for 2 min at room temperature. Then to this, we added potassium carbonate (34.5 g, 250.1 mmol) and refluxed for 36 h. Next, the mixture was filtered and the filtrate was concentrated to obtain a yellow liquid. This was extracted with ethyl acetate, and washed with water. The organic layers were combined and dried over $Na_2SO_4$, and purified by column chromatography using 4% ethyl acetate in petroleum ether as the eluent.

Yield: 13.02 g (76%). bp: 250° C. $^1$H NMR (300 MHz, $CDCl_3$, δ ppm, J Hz): 1.28 (t, 6H, J=7.6), 1.38 (m, 2H), 1.62 (q, 2H, J=7.2), 1.98 (q, 2H, J=7.7), 2.05 (s, 3H), 3.34 (t, 1H, J=7.7), 4.09 (t, 2H, J=6.6), 4.22 (q, 4H, J=7.2). $^{13}$C NMR (75 MHz, $CDCl_3$, δ ppm): 14.06, 20.79, 23.74, 28.25, 28.25, 51.84, 61.27, 63.89, 169.31, 171.11. IR ($CHCl_3$): 2982, 1728, 1463, 1367, 1233, 1151, 1029, and 860 cm$^{-1}$.

Synthesis of 2-(4-hydroxy butyl)-malonic acid (4)

2-(4-acetoxy-butyl)-malonic acid diethyl ester 3 (5.0 g, 18.25 mmol, see Section S1 in the Supporting Information for the synthesis of compound 3) was taken in a 100 mL round bottom flask containing methanol (50 mL) and stirred at room temperature for 2 min. To this was added NaOH (2.1 g, 54.74 mmol) in water (7 mL) and stirred at 90° C. for 8 h. The reaction mixture was shifted to room temperature and acidified (pH 2-3) with the drop-wise addition of dilute hydrochloric acid at room temperature with constant stirring. The mixture was then concentrated by using rotary evaporator and applying vacuum. To this was added chloroform (50 mL) and Argon gas was bubbled through the solution at 60° C. to remove excess HCl. The mixture was filtered and the filtrate was concentrated. This was then purified by column chromatography using 35% ethyl acetate in petroleum ether as eluent.

Yield: 2.31 g (72%). $^1$H NMR (300 MHz, $CDCl_3$, δ ppm, J Hz): 1.41 (m, 2H), 1.59 (m, 2H), 1.91 (q, 2H, $J_1$=7.3, $J_2$=7.8), 3.37 (t, 1H, J=7.4), 3.64 (t, 2H, J=6.5), 5.54 (bs, 1H). $^{13}$C NMR (75 MHz, $CDCl_3$, δ ppm): 23.53, 28.52, 31.75, 52.64, 62.11, 170.55. IR ($CHCl_3$): 3507, 2941, 1710, 1626, 1459, 1438, 1391, 1198, 1157, 1050, 947, 772, 741, 664 cm$^{-1}$.

Synthesis of Hyperbranched Polyester (HBPE) 5

The monomer 4 and the catalyst p-toluene sulphonic acid (100:1 molar ratio) were taken in a 10 mL round bottom flask and dried under high vacuum followed by the release of vacuum using dry argon gas. Then the flask was slowly heated to 150° C. under argon atmosphere using an oil bath and it was kept at this temperature for 2 h. The evolution of the byproduct (water vapor) was clearly visible after the sample was heated at 150° C. The melt was evacuated at 0.2 mm/Hg for 1 h while maintaining the same polymerization temperature. The polymer was purified by dissolving in DMF and reprecipitating in methanol. This was then centrifuged, washed with methanol and dried in a high vacuum pump to get pure polymer.

Yield: 65%. $^1$H NMR (300 MHz, DMSO-$d_6$, δ ppm): 1.25 (m, 2H), 1.52 (m, 2H), 1.67 (m, 2H), 3.38 (m, 1H), 3.58 (m, 2H), 5.28 (m, 1H). $^{13}$C NMR (75 MHz, DMSO-$d_6$, δ ppm): 23.82, 28.23, 51.85, 52.63, 65.37, 170.45. IR: 2954, 1727, 1458, 1436, 1343, 1218, 1152, 1054, 943, 858, 743, 694 cm$^{-1}$. TGA: 10% weight loss at 250° C.

Synthesis of Hyperbranched Polyester Amine (HBPE-EDA) 6: Carbodiimide Chemisrty

The polymer 5 (0.1 g, 0.0025 mmol) was dissolved in anhydrous DMF (1 mL) using vortex mixture and to this was added 1,1'-carbonyldiimidazole CDI (0.041 g, 0.25 mmol) in anhydrous DMF (0.1 mL) drop-wise. The reaction mixture was incubated for 2 h at room temperature. To this was then added ethylenediamine (0.015 g, 0.25 mmol) in anhydrous DMF (0.4 mL) drop-wise and incubated at room temperature for 24 h. The resulting reaction mixture was then precipitated in methanol, centrifuged and dried in a vacuum pump to get pure aminated polymer.

Yield: 88%. $^1$H NMR (300 MHz, DMSO-$d_6$, δ ppm): 1.27 (m, 2H), 1.55 (m, 2H), 1.74 (m, 2H), 2.26 (m, 4H), 2.88 (m, 4H), 3.34 (m, 1H), 3.63 (m, 4H), 4.04 (m, 2H). IR: 3245, 2940, 2864, 1725, 1659, 1534, 1435, 1240, 1159, 1062, 1021, 952, 929, 826, 749, 704, 663 cm$^{-1}$.

Synthesis of Clickable Hyperbranched Polyester (HBPE-PA) 7: Carbodiimide Chemistry Similar procedure has been followed as described for the synthesis of polymer 6. Instead of ethylenediamine, propargylamine (0.014 g, 0.25 mmol) was used as the starting material.

Yield: 80%. $^1$H NMR (500 MHz, DMSO-d$_6$, δ ppm): 1.28 (m, 2H), 1.54 (m, 2H), 1.75 (m, 2H), 2.25 (m, 2H), 3.42 (bs, 1H), 3.96 (m, 4H), 4.03 (m, 2H). IR: 3121, 2938, 2864, 2698, 2607, 1725, 1664, 1530, 1458, 1437, 1388, 1326, 1254, 1158, 1094, 1062, 929, 827, 748, 662 cm$^{-1}$.

General Procedures for the Synthesis of Functional Polymeric Nanoparticles Dye-Encapsulating PNPs (8-10): Solvent Diffusion Method Different near IR dye (DiI, DiR or DiD) solutions were prepared by mixing 5 μL of the dye aliquot (10 μg/μL) in 250 μL of DMF. The polymers (5, 6 or 7, 0.025 g) were dissolved in 250 μL of anydrous DMF using a vortex mixturer and mixed seperately with different dye solution. The resulting polymer-dye mixture in DMF was added drop-wise to deionized water (5 mL) with continuous stirring at room temperature forming dye encapsulated polymeric nanoparticle. The nanoparticle solution was dialyzed (using 6-8 K molecular weight cut off dialysis bag) three times against deionized water and phosphate buffered saline (PBS) solution.

Paclitaxel (Taxol@) and DiI co-encapsulating polymeric nanoparticles 10d

Taxol® (5 μL, 1 mg/mL) and DiI dye (5 μL, 10 μg/μL) were taken in an Eppendorf Tube® containing propargylated polymer (7, 0.025 g) in 500 μL DMF and followed the solvent diffusion method as described above.

AZT and DiI Co-Encapsulating Polymeric Nanoparticles 10e

AZT (azidothymidine) was dissolved in DMF to a final concentration of 1 mg/mL. The polymers (5 or 7, 0.025 g) were dissolved in 250 μL of DMF using a vortexer. Subsequently, AZT (5 μL, 1 mg/mL) and DiI (5 μL, 10 μg/mL) were added to the polymer solutions, followed by vortexing. The resulting polymer-AZT-DiI mixture in DMF was added dropwise to deionized water (5 mL) with continuous stirring at room temperature forming DiI and AZT co-encapsulating polymeric nanoparticles. The nanoparticle solutions were dialyzed (using 6-8 K molecular weight cut off dialysis bag) three times against deionized water and phosphate buffered saline (PBS) solution.

Synthesis of Aminopropylazide 12

Chloropropyl amine (7.0 g, 75.26 mmol) and sodium azide (14.23 g, 225.81 mmol) were taken in a 100 mL round bottom flask containing 40 mL of distilled water and heated at 80° C. for 20 h. The reaction mixture was concentrated via a rotavapor using high vacuum, and 2 g of KOH was added to it and then extracted by using diethyl ether. Subsequently, the reaction mixture was dried over anhydrous sodium sulphate and concentrated. Then, the mixture was purified through flash column chromatography using 4% ethyl acetate in petrolium ether as an eluant, in order to obtain the pure aminopropylazide.

Yield: 5.1 g (68%). $^1$H NMR (300 MHz, CDCl$_3$, δ ppm): 1.26 (bs, 2H), 1.81 (m, 2H), 2.80 (t, 2H), 3.38 (t, 2H). IR (CHCl$_3$): 3307, 2941, 2089, 1663, 1433, 1370, 1259, 1242, 1075, 1026, 818, 760 cm$^{-1}$.

Synthesis of Azide-Functionalized Folic Acid 13

1,1'-carbonyldiimidazole CDI (0.022 g, 0.014 mmol) was taken in an Eppendorf Tube® containing folic acid (0.05 g, 0.011 mmol) in anhydrous DMF (2 mL) and incubated for 2 h at 35° C. To this we added aminopropylazide (0.014 g, 0.014 mmol) in anhydrous DMF (100 μL) and incubated it for 24 h at room temperature. The reaction mixture was then cetrifuged and washed to remove excess starting materials. Finally, we dissolved the azide-functionalized folic acid in 1 mL of DMF. The presence of a band at 2091 cm$^{-1}$ in the IR spectrum and a UV absorbance shoulder at 354 nm confirmed the formation of azide-functionalized folic acid.

Yield: 0.05 g (86%). $^1$H NMR (400 MHz, DMSO-d$_6$, δ ppm): 1.61 (m, 2H), 1.65 (m, 2H), 1.90 (m, 2H), 2.19 (t, 2H), 2.78 (t, 2H), 4.18 (q, 1H), 4.21 (d, 2H), 6.62 (d, 2H), 7.59 (d, 2H), 8.58 (s, 1H). FT-IR (Neat): 3024, 2097, 1685, 1603, 1492, 1375, 1291, 1248, 1180, 1122, 1062, 950, 844, 755, 696 cm$^{-1}$.

Synthesis of Folate-Functionalized PNPs 11a-e: Click Chemisrty

The propargylated polymeric nanoparticles 10a-e (0.025 g, 6×10$^{-3}$ mmol) in bicarbonate buffer (pH=8.5) were taken to an eppendorf containing catalytic amount of CuI (0.11 μg, 6×10$^{-10}$ mmol) in 250 μL of bicarbonate buffer, vortexed for 30 seconds. To this was added azide-functionalized folic acid (13, 0.003 g, 6×10$^{-2}$ mmol) in DMSO and the reaction was incubated at room temperature for 12 h. The final reaction mixture was purified by dialysis using 6-8 K molecular weight cut off dialysis bag, against deionized water and phosphate buffered saline (PBS) solution. The purified functional PNPs (11a-e) were stored in refrigerator for further characterization.

Cell Culture and Cell Viability Studies

Lung carcinoma cells (A549) were grown in Kaighn's modification of Ham's F12 medium (F12K-Cellgro), supplemented with 5% fetal bovine serum (Heat-inactivated FBS-Cellgro), L-glutamine, streptomycin, amphotericin B, and sodium bicarbonate. The cells were maintained at 37° C., 5% CO$_2$ in a humidified incubator. We used the MTT assay in order to assess potential cytotoxic effects upon in vitro administration of the drug/dye—encapsulating functional HBPE nanoparticles. Specifically, lung carcinoma cells (3000 cells/well) were seeded in 96-well plates, and were incubated with the nanoparticles for 3 hours at 37° C. Then, each well was washed three times with 1×PBS and treated with 20 μl MTT (5 μg/μl, 3-(4,5-dimethylthiazol-2-yl)-2,5-diphenyltetrazo-lium bromide, Sigma-Aldrich) for 2 hours. The resulting formazan crystals were dissolved in acidified isopropanol (0.1 N HCl) and the absorbance was recoded at 570 nm and 750 nm (background), using a Synergy HT multi-detection microplate reader (Biotek). These experiments were performed in triplicates.

Cellular Internalization

Initially, in vitro uptake and internalization of the PNPs was assessed through fluorescence laser-scanning confocal microscopy, using a Zeiss LSM 510 confocal microscope.

Specifically A549 cells ($10^3$) were incubated for the stated time period with the corresponding PNP preparation in a humidified incubator (37° C., 5% $CO_2$). Subsequently, the cells were thoroughly washed three times with 1×PBS and fixed with a 10% formalin. Nuclear staining with DAPI was performed as recommended by the supplier. Then, multiple confocal images were obtained, achieving a representative view of the cell-PNP interaction. Confirmation of the confocal studies was facilitated through FACS and IVIS analyses. For FACS, $10^5$ lung carcinoma cells were incubated for 6 hours with the corresponding PNP preparation. Then the cells were detached from the culture dish with 0.05% trypsin, and the resulting pellet was resuspended in 1 mL culture media. The cell suspension underwent flow cytometric analysis, using a BD FACSCalibur system, in order to quantify the cellular uptake of the synthesized PNPs. For the IVIS analysis, $10^5$ lung carcinoma cells were incubated for 6 hours with the corresponding PNP preparation, and then the supernatant was collected in eppendorf tubes. Subsequently, we thoroughly washed the cells with 1×PBS and detached them, as stated above. The resulting pellets were resuspended in 1 ml culture media. All Eppendorf Tubes® were examined simultaneously on a Xenogen IVIS sytem, using the following filer sets: DsRed (500-550 nm/575-650 nm for DiI), Cy5.5 (615-665 nm/695-770 nm for DiD) and ICG (710-760 nm/810-875 nm for DiR). All experiments were performed in triplicates.

In vitro drug/dye release:

The in vitro drug/dye release studies were carried out using a dynamic dialysis technique at 37° C. Briefly, 100 μL of PNPs (11d) are incubated with a porcine liver esterase (20 μL) inside a dialysis bag (MWCO 6000-8000), which is then placed in a PBS solution (pH 7.4). The amount of guest (dye or drug) molecules released from the nanoparticle into the PBS solution was determined at regular time intervals by taking 1 mL aliquots from the PBS solution and measuring the fluorescence intensity at 575 nm for DiI and 372 nm for Taxol®®. The concentration of the either dye or drug was calculated using a standard calibration curve. The cumulative fraction of release versus time was calculated using the following equation:

Cumulative release(%)=[guest]$_t$/[guest]$_{total}$×100

Where [guest]$_t$ is the amount of guest released at time t, [guest]$_{total}$ is the total guest present in the guest encapsulated PNPs.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES CITED

[1] M. Fischer, F. Vögtle, *Angew. Chem., Int. Ed. Engl.* 1999, 38, 884-905.
[2] Fréchet, J. M. J.; Henmi, M.; Gitsov, I.; Aoshima, S.; Leduc, M. R.; Grubbs, R. B. *Science* 1995, 269, 1080-1083.
[3] Bharathi, P.; Moore, J. S. *J. Am. Chem. Soc.* 1997, 119, 3391-3392.
[4] Magnusson, H.; Malmström, E.; Hult, A. *Macromolecules* 2000, 33, 3099-3104.
[5] Kataoka, K.; Kwon, G. S.; Yokoyama, M.; Okano, T.; Sakurai, Y. *J. Controlled Release* 1993, 24, 119-132.
[6] Fréchet, J. M. J.; Tomalia, D. A.; *Dendrimers and Other Dendritic Polymers*; John Wiley: New York, 2002.
[7] Flory, P. J. *J. Am. Chem. Soc.* 1952, 74, 2718.
[8] Chu, F.; Hawker, C. *J. Polym. Bull.* 1993, 30, 265.
[9] Stiriba, S-E.; Kautz, H.; Frey, H. *J. Am. Chem. Soc.* 2002, 124, 9698.
[10] Plummer, C. J. G.; Garamszegi, L.; Leterrier, Y.; Rodlert, M and Manson, J-A. E. *Chem. Mater.* 2002, 14, 486-488.
[11] Schmid, G. *Chem. Rev.* 1992, 92, 1709.
[12] Fonseca, C.; Simoes, S.; Gaspar, R. *J. Controlled Release* 2002, 83, 273-286.
[13] Gupte, A.; Ciftci, K. *Int. J. Pharm.* 2004, 276, 93-106.
[14] Sparreboom, A.; Baker, S. D.; Verweij, J. *J. Clin. Oncol.* 2005, 23, 7765-7767.
[15] J. R. McCarthy, J. M. Perez, C. Bruckner, R. Weissleder, *Nano Lett.* 2005, 5, 2552-2556.
[16] B. S. Packard, D. E. Wolf, *Biochemistry* 1985, 24, 5176-5181.
[17] Mitra, A.; Lin, S. *J. Pharm. Pharmacol.* 2003, 55, 895-902.
[18] E. Y. Sun, L. Josephson, R. Weissleder, *Molecular Imaging* 2006, 5, 122-128.
[19] H. C. Kolb, M. G. Finn, K. B. Sharpless, *Angew. Chem. Int. Ed. Engl.* 2001, 40, 2004-2021;
[20] M. A. White, J. A. Johnson, J. T. Koberstein, N. J. Turro, *J. Am. Chem. Soc.* 2006, 128, 11356-11357.

What is claimed is:

1. A polymer comprising the repeating unit

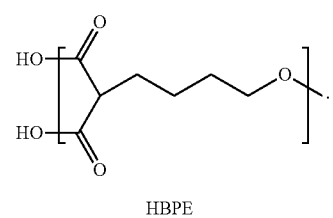

HBPE (5)

2. A polymeric nanoparticle comprising the polymer of claim 1.

3. The polymeric nanoparticle of claim 2, further comprising a hydrophobic near-infrared fluorescent dye encapsulated therein.

4. The polymeric nanoparticle of claim 3, wherein the dye is selected from the group consisting of DiI, DiR, DiD, and combinations thereof.

5. The polymeric nanoparticle of claim 2, further comprising a therapeutic drug encapsulated therein.

6. The polymeric nanoparticle of claim 5, further comprising a fluorescent dye co-encapsulated with said therapeutic drug.

7. The polymeric nanoparticle of claim 5, wherein the therapeutic drug comprises an anti-cancer drug.

8. The polymeric nanoparticle of claim 5, wherein the therapeutic drug comprises azidothymidine.

9. The polymeric nanoparticle of claim 2, wherein the polymeric nanoparticle is biodegradable.

10. The polymeric nanoparticle of claim 2, having one or more internal hydrophobic pockets and a hydrophilic outer surface.

11. The polymeric nanoparticle of claim 2, having an average diameter of 115±25 nm.

12. The polymeric nanoparticle of claim 2, being spherical in shape.

13. The polymeric nanoparticle of claim 2, having a negative zeta potential.

14. An aqueous suspension of the polymeric nanoparticle of claim 2.

15. The aqueous suspension of claim 14, further comprising a hydrophobic near-infrared fluorescent dye.

16. The aqueous suspension of claim 14, further comprising a therapeutic drug.

17. The aqueous suspension of claim 14, further comprising a hydrophobic near-infrared fluorescent dye and a therapeutic drug.

* * * * *